United States Patent
Miki et al.

(10) Patent No.: US 11,649,510 B2
(45) Date of Patent: May 16, 2023

(54) SCREENING METHOD FOR MATERIALS THAT SUPPRESS CHARACTERISTIC BODY ODOR OF ELDERLY PEOPLE

(71) Applicant: Takasago International Corporation, Tokyo (JP)

(72) Inventors: Azusa Miki, Kanagawa (JP); Ikuo Terada, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 341 days.

(21) Appl. No.: 16/956,889

(22) PCT Filed: Dec. 26, 2018

(86) PCT No.: PCT/JP2018/047918
§ 371 (c)(1),
(2) Date: Jun. 22, 2020

(87) PCT Pub. No.: WO2019/131789
PCT Pub. Date: Jul. 4, 2019

(65) Prior Publication Data
US 2020/0318205 A1 Oct. 8, 2020

(30) Foreign Application Priority Data
Dec. 27, 2017 (JP) .............................. JP2017-252587

(51) Int. Cl.
| C12Q 1/6897 | (2018.01) |
| G01N 33/50 | (2006.01) |
| G01N 33/68 | (2006.01) |
| G01N 33/74 | (2006.01) |
| G01N 33/497 | (2006.01) |

(52) U.S. Cl.
CPC ....... *C12Q 1/6897* (2013.01); *G01N 33/5008* (2013.01); *G01N 33/6872* (2013.01); *G01N 33/74* (2013.01); *G01N 33/497* (2013.01); *G01N 2333/705* (2013.01); *G01N 2333/726* (2013.01); *G01N 2500/02* (2013.01)

(58) Field of Classification Search
CPC ............. G01N 33/497; G01N 33/5008; G01N 33/6872; G01N 33/74; G01N 2333/705; G01N 2333/726; G01N 2500/02
See application file for complete search history.

(56) References Cited

U.S. PATENT DOCUMENTS

| 2010/0248390 A1 | 9/2010 | Matsunami et al. |
| 2013/0216492 A1 | 8/2013 | Kato et al. |
| 2013/0336910 A1 | 12/2013 | Chatelain et al. |
| 2014/0186864 A1 | 7/2014 | Kato et al. |
| 2018/0180600 A1 | 6/2018 | Yoshikawa et al. |

FOREIGN PATENT DOCUMENTS

| JP | 11-286423 A | 10/1999 |
| JP | 2011-178721 A | 9/2011 |
| JP | 2012-050411 A | 3/2012 |
| JP | 2012-249614 A | 12/2012 |
| JP | 2012-250958 A | 12/2012 |
| JP | 2014-240441 A | 12/2014 |
| WO | WO-2012/108495 A1 | 8/2012 |
| WO | WO-2016/204211 A1 | 12/2016 |

OTHER PUBLICATIONS

Hara et al., Effects of Cyclodextrins on Deodoration of "Aging Odor". Journal of Inclusion Phenomena and Macrocyclic Chemistry 44:241-245, 2002.*
Araneda et al., "The molecular receptive range of an odorant receptor," Nature Neuroscience, Dec. 2000, 3(12):1248-1255.
Kishimoto, Toru, "The recent findings in the off-flavors of beer," J. Japan Association of Odor Environment, 2013, 44(1):13-20, with English abstract on last page.
Araneda et al., "A pharmacological profile of the aldehyde receptor repertoire in rat olfactory epithelium," The Journal of Physiology, Jan. 14, 2004, 555(3):743-756.

* cited by examiner

*Primary Examiner* — Ruixiang Li
(74) *Attorney, Agent, or Firm* — Foley & Lardner LLP

(57) ABSTRACT

The present invention relates to a screening method for materials that suppress the characteristic body odor of elderly people. The screening method of the present invention is designed such that test substances are screened with olfactory receptors responsive to substances responsible for the characteristic body odor of elderly people to select candidate substances for materials that suppress the characteristic body odor of elderly people, and this method comprises adding a test substance and a substance responsible for the characteristic body odor of elderly people to at least one olfactory receptor polypeptide selected from the group consisting of (a) OR2C1, OR2J2, OR4E2 and OR5P3, and (b) polypeptides which comprise an amino acid sequence sharing an identity of at least 80% with the amino acid sequence of any of the polypeptides in (a) and which are responsive to the substance responsible for the characteristic body odor of elderly people; measuring the response of the olfactory receptor polypeptide to the substance responsible for the characteristic body odor of elderly people; and identifying a test substance that suppresses the response of the olfactory receptor polypeptide on the basis of the measured response. Moreover, the present invention relates to a screening method for trans-2-nonenal odor suppressors and a screening method for trans-2-octenal odor suppressors.

9 Claims, 6 Drawing Sheets
Specification includes a Sequence Listing.

SEQUENCE LISTING

```
<160> NUMBER OF SEQ ID NOS: 22

<210> SEQ ID NO 1
<211> LENGTH: 939
<212> TYPE: DNA
<213> ORGANISM: Homo sapiens
<220> FEATURE:
<221> NAME/KEY: CDS
<222> LOCATION: (1)..(939)

<400> SEQUENCE: 1 atg gac ggg gtg aat gat agc tcc ttg cag ggc ttt gtt ctg atg ggc      48
Met Asp Gly Val Asn Asp Ser Ser Leu Gln Gly Phe Val Leu Met Gly
1               5                   10                  15 ata tca gac cat ccc cag ctg gag atg atc ttt ttt ata gcc atc ctc      96
Ile Ser Asp His Pro Gln Leu Glu Met Ile Phe Phe Ile Ala Ile Leu
                20                  25                  30 ttc tcc tat ttg ctg acc cta ctt ggg aac tca acc atc atc ttg ctt     144
Phe Ser Tyr Leu Leu Thr Leu Leu Gly Asn Ser Thr Ile Ile Leu Leu
            35                  40                  45 tcc cgc ctg gag gcc cgg ctc cat aca ccc atg tac ttc ttc ctc agc     192
Ser Arg Leu Glu Ala Arg Leu His Thr Pro Met Tyr Phe Phe Leu Ser
        50                  55                  60 aac ctc tcc tcc ttg gac ctt gct ttc gct act agt tca gtc ccc caa     240
Asn Leu Ser Ser Leu Asp Leu Ala Phe Ala Thr Ser Ser Val Pro Gln
65                  70                  75                  80 atg ctg atc aat tta tgg gga cca ggc aag acc atc agc tat ggt ggc     288
Met Leu Ile Asn Leu Trp Gly Pro Gly Lys Thr Ile Ser Tyr Gly Gly
                85                  90                  95 tgc ata acc cag ctc tat gtc ttc ctt tgg ctg ggg gcc acc gag tgc     336
Cys Ile Thr Gln Leu Tyr Val Phe Leu Trp Leu Gly Ala Thr Glu Cys
                100                 105                 110 atc ctg ctg gtg gtg atg gca ttt gac cgc tac gtg gca gtg tgc cgg     384
Ile Leu Leu Val Val Met Ala Phe Asp Arg Tyr Val Ala Val Cys Arg
```

```
                115                    120                    125
ccc ctc cgc tac acc gcc atc atg aac ccc cag ctc tgc tgg ctg ctg      432
Pro Leu Arg Tyr Thr Ala Ile Met Asn Pro Gln Leu Cys Trp Leu Leu
    130                    135                    140 gct gtg att gcc tgc ctg ggt ggc ttg ggc aac tct gtg atc cag tca      480
Ala Val Ile Ala Cys Leu Gly Gly Leu Gly Asn Ser Val Ile Gln Ser
145                    150                    155                160 aca ttc act ctg cag ctc cca ttg tgt ggg cac cgg agg gtg gag gga      528
Thr Phe Thr Leu Gln Leu Pro Leu Cys Gly His Arg Arg Val Glu Gly
                165                    170                    175 ttc ctc tgc gag gtg cct gcc atg atc aaa ctg gcc tgt ggc gac aca      576
Phe Leu Cys Glu Val Pro Ala Met Ile Lys Leu Ala Cys Gly Asp Thr
            180                    185                    190 agt ctc aac cag gct gtg ctc aat ggt gtc tgc acc ttc ttc act gca      624
Ser Leu Asn Gln Ala Val Leu Asn Gly Val Cys Thr Phe Phe Thr Ala
        195                    200                    205 gtc cca cta agc atc atc gtg atc tcc tac tgc ctc att gct cag gca      672
Val Pro Leu Ser Ile Ile Val Ile Ser Tyr Cys Leu Ile Ala Gln Ala
    210                    215                    220 gtg ctg aaa atc cgc tct gca gag ggg agg cga aag gcg ttc aat acg      720
Val Leu Lys Ile Arg Ser Ala Glu Gly Arg Arg Lys Ala Phe Asn Thr
225                    230                    235                240 tgc ctc tcc cat ctg ctg gtg gtg ttc ctc ttc tat ggc tca gcc agc      768
Cys Leu Ser His Leu Leu Val Val Phe Leu Phe Tyr Gly Ser Ala Ser
                245                    250                    255 tat ggg tat ctg ctt ccg gcc aag aac agc aaa cag gac cag ggc aag      816
Tyr Gly Tyr Leu Leu Pro Ala Lys Asn Ser Lys Gln Asp Gln Gly Lys
            260                    265                    270 ttc att tcc ctg ttc tac tcg ttg gtc aca ccc atg gtg aat ccc ctc      864
Phe Ile Ser Leu Phe Tyr Ser Leu Val Thr Pro Met Val Asn Pro Leu
        275                    280                    285 atc tac acg ctg cgg aac atg gaa gtg aag ggc gca ctg agg agg ttg      912
Ile Tyr Thr Leu Arg Asn Met Glu Val Lys Gly Ala Leu Arg Arg Leu
    290                    295                    300 ctg ggg aaa gga aga gaa gtt ggc tga                                  939
Leu Gly Lys Gly Arg Glu Val Gly
305                    310

<210> SEQ ID NO 2
<211> LENGTH: 312
<212> TYPE: PRT
<213> ORGANISM: Homo sapiens

<400> SEQUENCE: 2

Met Asp Gly Val Asn Asp Ser Ser Leu Gln Gly Phe Val Leu Met Gly
1               5                   10                  15

Ile Ser Asp His Pro Gln Leu Glu Met Ile Phe Phe Ile Ala Ile Leu
            20                  25                  30

Phe Ser Tyr Leu Leu Thr Leu Leu Gly Asn Ser Thr Ile Ile Leu Leu
        35                  40                  45

Ser Arg Leu Glu Ala Arg Leu His Thr Pro Met Tyr Phe Phe Leu Ser
    50                  55                  60

Asn Leu Ser Ser Leu Asp Leu Ala Phe Ala Thr Ser Ser Val Pro Gln
65                  70                  75                  80

Met Leu Ile Asn Leu Trp Gly Pro Gly Lys Thr Ile Ser Tyr Gly Gly
                85                  90                  95

Cys Ile Thr Gln Leu Tyr Val Phe Leu Trp Leu Gly Ala Thr Glu Cys
            100                 105                 110
```

-continued

```
Ile Leu Leu Val Val Met Ala Phe Asp Arg Tyr Val Ala Val Cys Arg
            115                 120                 125

Pro Leu Arg Tyr Thr Ala Ile Met Asn Pro Gln Leu Cys Trp Leu Leu
130                 135                 140

Ala Val Ile Ala Cys Leu Gly Gly Leu Gly Asn Ser Val Ile Gln Ser
145                 150                 155                 160

Thr Phe Thr Leu Gln Leu Pro Leu Cys Gly His Arg Arg Val Glu Gly
                165                 170                 175

Phe Leu Cys Glu Val Pro Ala Met Ile Lys Leu Ala Cys Gly Asp Thr
            180                 185                 190

Ser Leu Asn Gln Ala Val Leu Asn Gly Val Cys Thr Phe Phe Thr Ala
            195                 200                 205

Val Pro Leu Ser Ile Ile Val Ile Ser Tyr Cys Leu Ile Ala Gln Ala
            210                 215                 220

Val Leu Lys Ile Arg Ser Ala Glu Gly Arg Arg Lys Ala Phe Asn Thr
225                 230                 235                 240

Cys Leu Ser His Leu Leu Val Val Phe Leu Phe Tyr Gly Ser Ala Ser
                245                 250                 255

Tyr Gly Tyr Leu Leu Pro Ala Lys Asn Ser Lys Gln Asp Gln Gly Lys
                260                 265                 270

Phe Ile Ser Leu Phe Tyr Ser Leu Val Thr Pro Met Val Asn Pro Leu
            275                 280                 285

Ile Tyr Thr Leu Arg Asn Met Glu Val Lys Gly Ala Leu Arg Arg Leu
            290                 295                 300

Leu Gly Lys Gly Arg Glu Val Gly
305                 310
```

<210> SEQ ID NO 3
<211> LENGTH: 939
<212> TYPE: DNA
<213> ORGANISM: Homo sapiens
<220> FEATURE:
<221> NAME/KEY: CDS
<222> LOCATION: (1)..(939)

<400> SEQUENCE: 3

```
atg atg att aaa aaa aat gca agt tcg gaa gac ttc ttt att cta ctt    48
Met Met Ile Lys Lys Asn Ala Ser Ser Glu Asp Phe Phe Ile Leu Leu
1               5                   10                  15 gga ttt tct aat tgg cct cag ctg gaa gta gtt ctc ttt gtg gtt atc    96
Gly Phe Ser Asn Trp Pro Gln Leu Glu Val Val Leu Phe Val Val Ile
                20                  25                  30 ttg atc ttc tac ctg atg aca ctg aca gga aac ctg ttc atc atc atc   144
Leu Ile Phe Tyr Leu Met Thr Leu Thr Gly Asn Leu Phe Ile Ile Ile
            35                  40                  45 ctg tca tac gtg gac tcc cat ctc cac aca cca atg tac ttc ttc ctt   192
Leu Ser Tyr Val Asp Ser His Leu His Thr Pro Met Tyr Phe Phe Leu
        50                  55                  60 tca aac ctc tca ttt ctg gat ctc tgc tac acc acc agc tct atc cct   240
Ser Asn Leu Ser Phe Leu Asp Leu Cys Tyr Thr Thr Ser Ser Ile Pro
65                  70                  75                  80 cag ttg ctg gtg aat ctc cgg ggc ccg gaa aag acc atc tcg tat gct   288
Gln Leu Leu Val Asn Leu Arg Gly Pro Glu Lys Thr Ile Ser Tyr Ala
                85                  90                  95 ggt tgc atg gtt caa ctt tac ttt gtt ctt gca ctg gga atc aca gag   336
Gly Cys Met Val Gln Leu Tyr Phe Val Leu Ala Leu Gly Ile Thr Glu
            100                 105                 110 tgt gtc cta ctg gtg gtg atg tca tat gat cgt tat gta gct gtg tgt   384
Cys Val Leu Leu Val Val Met Ser Tyr Asp Arg Tyr Val Ala Val Cys
```

```
                Cys Val Leu Val Val Met Ser Tyr Asp Arg Tyr Ala Val Cys
                        115                 120                 125 aga cct ttg cat tac act gtc ctc atg cac cct cgt ttc tgc cac ttg    432
Arg Pro Leu His Tyr Thr Val Leu Met His Pro Arg Phe Cys His Leu
130                 135                 140 ttg gtt gcg gct tct tgg gta att ggt ttt act atc tca gca ctt cat    480
Leu Val Ala Ala Ser Trp Val Ile Gly Phe Thr Ile Ser Ala Leu His
145                 150                 155                 160 tcc tcc ttt act ttc tgg gta ccc ctt tgt gga cat cgc cta gtg gat    528
Ser Ser Phe Thr Phe Trp Val Pro Leu Cys Gly His Arg Leu Val Asp
                165                 170                 175 cac ttc ttc tgt gaa gtt cca gca ctt ctg cgt tta tca tgt gtt gac    576
His Phe Phe Cys Glu Val Pro Ala Leu Leu Arg Leu Ser Cys Val Asp
                180                 185                 190 acc cat gca aat gag ctg acc ctc atg gtc atg agc tcc att ttt gtt    624
Thr His Ala Asn Glu Leu Thr Leu Met Val Met Ser Ser Ile Phe Val
                195                 200                 205 ctc ata cct ctc att ctc att ctc act acc tat ggt gcc att gcc cgg    672
Leu Ile Pro Leu Ile Leu Ile Leu Thr Thr Tyr Gly Ala Ile Ala Arg
210                 215                 220 gct gta ctg agc atg caa tca acc act ggg ctt cag aaa gtg ttt agg    720
Ala Val Leu Ser Met Gln Ser Thr Thr Gly Leu Gln Lys Val Phe Arg
225                 230                 235                 240 aca tgt gga gcc cat ctt atg gtt gta tct ctc ttt ttc att cca gtc    768
Thr Cys Gly Ala His Leu Met Val Val Ser Leu Phe Phe Ile Pro Val
                245                 250                 255 atg tgc atg tat ctc cag cca cca tca gaa aat tct cct gat cag ggc    816
Met Cys Met Tyr Leu Gln Pro Pro Ser Glu Asn Ser Pro Asp Gln Gly
                260                 265                 270 aag ttc att gcc ctc ttt tat act gtt gtc aca ccg agt ctt aat cct    864
Lys Phe Ile Ala Leu Phe Tyr Thr Val Val Thr Pro Ser Leu Asn Pro
                275                 280                 285 cta atc tac act ctc aga aac aag cat gta aaa ggg gca gcg aag aga    912
Leu Ile Tyr Thr Leu Arg Asn Lys His Val Lys Gly Ala Ala Lys Arg
                290                 295                 300 cta ttg ggg tgg gag tgg ggg aag tga                                939
Leu Leu Gly Trp Glu Trp Gly Lys
305                 310

<210> SEQ ID NO 4
<211> LENGTH: 312
<212> TYPE: PRT
<213> ORGANISM: Homo sapiens

<400> SEQUENCE: 4

Met Met Ile Lys Lys Asn Ala Ser Ser Glu Asp Phe Phe Ile Leu Leu
1               5                   10                  15

Gly Phe Ser Asn Trp Pro Gln Leu Glu Val Val Leu Phe Val Val Ile
                20                  25                  30

Leu Ile Phe Tyr Leu Met Thr Leu Thr Gly Asn Leu Phe Ile Ile Ile
                35                  40                  45

Leu Ser Tyr Val Asp Ser His Leu His Thr Pro Met Tyr Phe Phe Leu
        50                  55                  60

Ser Asn Leu Ser Phe Leu Asp Leu Cys Tyr Thr Thr Ser Ser Ile Pro
65              70                  75                  80

Gln Leu Leu Val Asn Leu Arg Gly Pro Glu Lys Thr Ile Ser Tyr Ala
                85                  90                  95

Gly Cys Met Val Gln Leu Tyr Phe Val Leu Ala Leu Gly Ile Thr Glu
                100                 105                 110
```

```
Cys Val Leu Leu Val Val Met Ser Tyr Asp Arg Tyr Val Ala Val Cys
            115                 120                 125

Arg Pro Leu His Tyr Thr Val Leu Met His Pro Arg Phe Cys His Leu
130                 135                 140

Leu Val Ala Ala Ser Trp Val Ile Gly Phe Thr Ile Ser Ala Leu His
145                 150                 155                 160

Ser Ser Phe Thr Phe Trp Val Pro Leu Cys Gly His Arg Leu Val Asp
                165                 170                 175

His Phe Phe Cys Glu Val Pro Ala Leu Leu Arg Leu Ser Cys Val Asp
            180                 185                 190

Thr His Ala Asn Glu Leu Thr Leu Met Val Met Ser Ser Ile Phe Val
            195                 200                 205

Leu Ile Pro Leu Ile Leu Ile Leu Thr Thr Tyr Gly Ala Ile Ala Arg
        210                 215                 220

Ala Val Leu Ser Met Gln Ser Thr Thr Gly Leu Gln Lys Val Phe Arg
225                 230                 235                 240

Thr Cys Gly Ala His Leu Met Val Val Ser Leu Phe Phe Ile Pro Val
                245                 250                 255

Met Cys Met Tyr Leu Gln Pro Pro Ser Glu Asn Ser Pro Asp Gln Gly
            260                 265                 270

Lys Phe Ile Ala Leu Phe Tyr Thr Val Thr Pro Ser Leu Asn Pro
        275                 280                 285

Leu Ile Tyr Thr Leu Arg Asn Lys His Val Lys Gly Ala Ala Lys Arg
        290                 295                 300

Leu Leu Gly Trp Glu Trp Gly Lys
305                 310

<210> SEQ ID NO 5
<211> LENGTH: 942
<212> TYPE: DNA
<213> ORGANISM: Homo sapiens
<220> FEATURE:
<221> NAME/KEY: CDS
<222> LOCATION: (1)..(942)

<400> SEQUENCE: 5 atg gac agt cta aac caa aca aga gtg act gaa ttt gtc ttc ttg gga    48
Met Asp Ser Leu Asn Gln Thr Arg Val Thr Glu Phe Val Phe Leu Gly
1               5                   10                  15 ctc act gat aac cgg gtg ctg gaa atg ctg ttt ttc atg gca ttc tca    96
Leu Thr Asp Asn Arg Val Leu Glu Met Leu Phe Phe Met Ala Phe Ser
                20                  25                  30 gcc att tat atg cta acg ctt tcg ggg aac att ctc atc atc att gcc   144
Ala Ile Tyr Met Leu Thr Leu Ser Gly Asn Ile Leu Ile Ile Ile Ala
            35                  40                  45 aca gtc ttt act cca agt ctc cat acc ccc atg tat ttc ttc ctg agc   192
Thr Val Phe Thr Pro Ser Leu His Thr Pro Met Tyr Phe Phe Leu Ser
    50                  55                  60 aat ctg tcc ttt att gac atc tgc cac tca tct gtc act gtg cct aag   240
Asn Leu Ser Phe Ile Asp Ile Cys His Ser Ser Val Thr Val Pro Lys
65                  70                  75                  80 atg ttg gag ggt ttg ctt tta gaa aga aag acc att tcc ttt gac aac   288
Met Leu Glu Gly Leu Leu Leu Glu Arg Lys Thr Ile Ser Phe Asp Asn
                85                  90                  95 tgc atc aca cag ctc ttc ttc cta cat ctc ttt gcc tgt gcc gag atc   336
Cys Ile Thr Gln Leu Phe Phe Leu His Leu Phe Ala Cys Ala Glu Ile
            100                 105                 110
```

-continued

| | | |
|---|---|---|
| ttt ctg ctg atc att atg gcg tat gat cgt tac gtg gct atc tgc act<br>Phe Leu Leu Ile Ile Met Ala Tyr Asp Arg Tyr Val Ala Ile Cys Thr<br>    115                 120                 125 | | 384 |
| cca ctc cac tac ccc aat gtg atg aac atg aga gtc tgt ata cag ctt<br>Pro Leu His Tyr Pro Asn Val Met Asn Met Arg Val Cys Ile Gln Leu<br>    130                 135                 140 | | 432 |
| gtc ttt gct ctc tgg ttg ggg gtt act gtt cac tca cta ggg cag acc<br>Val Phe Ala Leu Trp Leu Gly Gly Thr Val His Ser Leu Gly Gln Thr<br>145                 150                 155                 160 | | 480 |
| ttc ttg act att cgt cta cct tac tgt ggc ccc aac att att gac agc<br>Phe Leu Thr Ile Arg Leu Pro Tyr Cys Gly Pro Asn Ile Ile Asp Ser<br>    165                 170                 175 | | 528 |
| tac ttc tgt gat gtg cct ctt gtt atc aag ctg gcc tgc aca gat aca<br>Tyr Phe Cys Asp Val Pro Leu Val Ile Lys Leu Ala Cys Thr Asp Thr<br>    180                 185                 190 | | 576 |
| tac ctc aca gga ata ctg att gtg acc aat agt gga acc atc tcc ctc<br>Tyr Leu Thr Gly Ile Leu Ile Val Thr Asn Ser Gly Thr Ile Ser Leu<br>    195                 200                 205 | | 624 |
| tcc tgt ttc ttg gcc gtg gtc acc tcc tat atg gtc atc ctg gtt tct<br>Ser Cys Phe Leu Ala Val Val Thr Ser Tyr Met Val Ile Leu Val Ser<br>210                 215                 220 | | 672 |
| ctt cga aaa cac tca gct gaa ggg cgc cgg aaa gcc ctg tct acc tgc<br>Leu Arg Lys His Ser Ala Glu Gly Arg Arg Lys Ala Leu Ser Thr Cys<br>225                 230                 235                 240 | | 720 |
| tcg gcc cac ttc atg gtg gtt gcc ctc ttc ttt ggg cca tgt atc ttc<br>Ser Ala His Phe Met Val Val Ala Leu Phe Phe Gly Pro Cys Ile Phe<br>    245                 250                 255 | | 768 |
| atc tat act cgg cca gac acc agc ttc tcc att gac aag gtg gtg tct<br>Ile Tyr Thr Arg Pro Asp Thr Ser Phe Ser Ile Asp Lys Val Val Ser<br>    260                 265                 270 | | 816 |
| gtc ttc tac aca gtg gtc acc cct ttg ctg aat ccc ttc att tac acc<br>Val Phe Tyr Thr Val Val Thr Pro Leu Leu Asn Pro Phe Ile Tyr Thr<br>    275                 280                 285 | | 864 |
| ttg agg aat gag gag gta aaa agt gcc atg aag cag ctc agg cag aga<br>Leu Arg Asn Glu Glu Val Lys Ser Ala Met Lys Gln Leu Arg Gln Arg<br>    290                 295                 300 | | 912 |
| caa gtt ttt ttc acg aaa tca tat aca taa<br>Gln Val Phe Phe Thr Lys Ser Tyr Thr<br>305                 310 | | 942 |

<210> SEQ ID NO 6
<211> LENGTH: 313
<212> TYPE: PRT
<213> ORGANISM: Homo sapiens

<400> SEQUENCE: 6

Met Asp Ser Leu Asn Gln Thr Arg Val Thr Glu Phe Val Phe Leu Gly
1               5                   10                  15

Leu Thr Asp Asn Arg Val Leu Glu Met Leu Phe Phe Met Ala Phe Ser
                20                  25                  30

Ala Ile Tyr Met Leu Thr Leu Ser Gly Asn Ile Leu Ile Ile Ile Ala
            35                  40                  45

Thr Val Phe Thr Pro Ser Leu His Thr Pro Met Tyr Phe Phe Leu Ser
        50                  55                  60

Asn Leu Ser Phe Ile Asp Ile Cys His Ser Ser Val Thr Val Pro Lys
65                  70                  75                  80

Met Leu Glu Gly Leu Leu Leu Glu Arg Lys Thr Ile Ser Phe Asp Asn
                85                  90                  95

Cys Ile Thr Gln Leu Phe Phe Leu His Leu Phe Ala Cys Ala Glu Ile

```
                    100                 105                 110
Phe Leu Leu Ile Ile Met Ala Tyr Asp Arg Tyr Val Ala Ile Cys Thr
            115                 120                 125

Pro Leu His Tyr Pro Asn Val Met Asn Met Arg Val Cys Ile Gln Leu
        130                 135                 140

Val Phe Ala Leu Trp Leu Gly Gly Thr Val His Ser Leu Gly Gln Thr
145                 150                 155                 160

Phe Leu Thr Ile Arg Leu Pro Tyr Cys Gly Pro Asn Ile Ile Asp Ser
                165                 170                 175

Tyr Phe Cys Asp Val Pro Leu Val Ile Lys Leu Ala Cys Thr Asp Thr
            180                 185                 190

Tyr Leu Thr Gly Ile Leu Ile Val Thr Asn Ser Gly Thr Ile Ser Leu
        195                 200                 205

Ser Cys Phe Leu Ala Val Val Thr Ser Tyr Met Val Ile Leu Val Ser
    210                 215                 220

Leu Arg Lys His Ser Ala Glu Gly Arg Arg Lys Ala Leu Ser Thr Cys
225                 230                 235                 240

Ser Ala His Phe Met Val Val Ala Leu Phe Phe Gly Pro Cys Ile Phe
                245                 250                 255

Ile Tyr Thr Arg Pro Asp Thr Ser Phe Ser Ile Asp Lys Val Val Ser
            260                 265                 270

Val Phe Tyr Thr Val Val Thr Pro Leu Leu Asn Pro Phe Ile Tyr Thr
        275                 280                 285

Leu Arg Asn Glu Glu Val Lys Ser Ala Met Lys Gln Leu Arg Gln Arg
    290                 295                 300

Gln Val Phe Phe Thr Lys Ser Tyr Thr
305                 310

<210> SEQ ID NO 7
<211> LENGTH: 936
<212> TYPE: DNA
<213> ORGANISM: Homo sapiens
<220> FEATURE:
<221> NAME/KEY: CDS
<222> LOCATION: (1)..(936)

<400> SEQUENCE: 7 atg ggg act gga aat gac acc act gtg gta gag ttt act ctt ttg ggg      48
Met Gly Thr Gly Asn Asp Thr Thr Val Val Glu Phe Thr Leu Leu Gly
1               5                   10                  15 tta tct gag gat act aca gtt tgt gct att tta ttt ctt gtg ttt cta      96
Leu Ser Glu Asp Thr Thr Val Cys Ala Ile Leu Phe Leu Val Phe Leu
                20                  25                  30 gga att tat gtt gtc acc tta atg ggt aat atc agc ata att gta ttg     144
Gly Ile Tyr Val Val Thr Leu Met Gly Asn Ile Ser Ile Ile Val Leu
            35                  40                  45 atc aga aga agt cat cat ctt cat aca ccc atg tac att ttc ctc tgc     192
Ile Arg Arg Ser His His Leu His Thr Pro Met Tyr Ile Phe Leu Cys
        50                  55                  60 cat ttg gcc ttt gta gac att ggg tac tcc tca tca gtc aca cct gtc     240
His Leu Ala Phe Val Asp Ile Gly Tyr Ser Ser Ser Val Thr Pro Val
65                  70                  75                  80 atg ctc atg agc ttc tta agg aaa gaa acc tct ctc cct gtt gct ggt     288
Met Leu Met Ser Phe Leu Arg Lys Glu Thr Ser Leu Pro Val Ala Gly
                85                  90                  95 tgt gtg gcc cag ctc tgt tct gta gtg acg ttt ggt acg gcc gag tgc     336
Cys Val Ala Gln Leu Cys Ser Val Val Thr Phe Gly Thr Ala Glu Cys
            100                 105                 110
```

```
ttc ctg ctg gct gcc atg gcc tat gat cgc tat gtg gcc atc tgc tca    384
Phe Leu Leu Ala Ala Met Ala Tyr Asp Arg Tyr Val Ala Ile Cys Ser
            115                 120                 125 ccc ctg ctc tac tct acc tgc atg tcc cct gga gtc tgc atc atc tta    432
Pro Leu Leu Tyr Ser Thr Cys Met Ser Pro Gly Val Cys Ile Ile Leu
        130                 135                 140 gtg ggc atg tcc tac ctg ggt gga tgt gtg aat gct tgg aca ttc att    480
Val Gly Met Ser Tyr Leu Gly Gly Cys Val Asn Ala Trp Thr Phe Ile
145                 150                 155                 160 ggc tgc tta tta aga ctg tcc ttc tgt ggg cca aat aaa gtc aat cac    528
Gly Cys Leu Leu Arg Leu Ser Phe Cys Gly Pro Asn Lys Val Asn His
                165                 170                 175 ttt ttc tgt gac tat tca cca ctt ttg aag ctt gct tgt tcc cat gat    576
Phe Phe Cys Asp Tyr Ser Pro Leu Leu Lys Leu Ala Cys Ser His Asp
            180                 185                 190 ttt act ttt gaa ata att cca gct atc tct tct gga tct atc att gtg    624
Phe Thr Phe Glu Ile Ile Pro Ala Ile Ser Ser Gly Ser Ile Ile Val
        195                 200                 205 gcc act gtg tgt gtc ata gcc ata tcc tac atc tat atc ctc atc acc    672
Ala Thr Val Cys Val Ile Ala Ile Ser Tyr Ile Tyr Ile Leu Ile Thr
210                 215                 220 atc ctg aag atg cac tcc acc aag ggc cgc cac aag gcc ttc tcc acc    720
Ile Leu Lys Met His Ser Thr Lys Gly Arg His Lys Ala Phe Ser Thr
225                 230                 235                 240 tgc acc tcc cac ctc act gca gtc act ctg ttc tat ggg acc att acc    768
Cys Thr Ser His Leu Thr Ala Val Thr Leu Phe Tyr Gly Thr Ile Thr
                245                 250                 255 ttc att tat gtg atg ccc aag tcc agc tac tca act gac cag aac aag    816
Phe Ile Tyr Val Met Pro Lys Ser Ser Tyr Ser Thr Asp Gln Asn Lys
            260                 265                 270 gtg gtg tct gtg ttc tac acc gtg gtg att ccc atg ttg aac ccc ctg    864
Val Val Ser Val Phe Tyr Thr Val Val Ile Pro Met Leu Asn Pro Leu
        275                 280                 285 atc tac agc ctc agg aac aag gag att aag ggg gct ctg aag aga gag    912
Ile Tyr Ser Leu Arg Asn Lys Glu Ile Lys Gly Ala Leu Lys Arg Glu
290                 295                 300 ctt aga ata aaa ata ttt tct tga                                    936
Leu Arg Ile Lys Ile Phe Ser
305                 310
```

<210> SEQ ID NO 8
<211> LENGTH: 311
<212> TYPE: PRT
<213> ORGANISM: Homo sapiens

<400> SEQUENCE: 8

```
Met Gly Thr Gly Asn Asp Thr Thr Val Val Glu Phe Thr Leu Leu Gly
1               5                   10                  15

Leu Ser Glu Asp Thr Thr Val Cys Ala Ile Leu Phe Leu Val Phe Leu
            20                  25                  30

Gly Ile Tyr Val Val Thr Leu Met Gly Asn Ile Ser Ile Val Leu
        35                  40                  45

Ile Arg Arg Ser His His Leu His Thr Pro Met Tyr Ile Phe Leu Cys
 50                  55                  60

His Leu Ala Phe Val Asp Ile Gly Tyr Ser Ser Ser Val Thr Pro Val
65                  70                  75                  80

Met Leu Met Ser Phe Leu Arg Lys Glu Thr Ser Leu Pro Val Ala Gly
            85                  90                  95
```

```
Cys Val Ala Gln Leu Cys Ser Val Val Thr Phe Gly Thr Ala Glu Cys
                100                 105                 110

Phe Leu Leu Ala Ala Met Ala Tyr Asp Arg Tyr Val Ala Ile Cys Ser
            115                 120                 125

Pro Leu Leu Tyr Ser Thr Cys Met Ser Pro Gly Val Cys Ile Ile Leu
        130                 135                 140

Val Gly Met Ser Tyr Leu Gly Gly Cys Val Asn Ala Trp Thr Phe Ile
145                 150                 155                 160

Gly Cys Leu Leu Arg Leu Ser Phe Cys Gly Pro Asn Lys Val Asn His
                165                 170                 175

Phe Phe Cys Asp Tyr Ser Pro Leu Leu Lys Leu Ala Cys Ser His Asp
            180                 185                 190

Phe Thr Phe Glu Ile Ile Pro Ala Ile Ser Ser Gly Ser Ile Ile Val
        195                 200                 205

Ala Thr Val Cys Val Ile Ala Ile Ser Tyr Ile Tyr Ile Leu Ile Thr
210                 215                 220

Ile Leu Lys Met His Ser Thr Lys Gly Arg His Lys Ala Phe Ser Thr
225                 230                 235                 240

Cys Thr Ser His Leu Thr Ala Val Thr Leu Phe Tyr Gly Thr Ile Thr
                245                 250                 255

Phe Ile Tyr Val Met Pro Lys Ser Ser Tyr Ser Thr Asp Gln Asn Lys
            260                 265                 270

Val Val Ser Val Phe Tyr Thr Val Ile Pro Met Leu Asn Pro Leu
        275                 280                 285

Ile Tyr Ser Leu Arg Asn Lys Glu Ile Lys Gly Ala Leu Lys Arg Glu
290                 295                 300

Leu Arg Ile Lys Ile Phe Ser
305                 310

<210> SEQ ID NO 9
<211> LENGTH: 939
<212> TYPE: DNA
<213> ORGANISM: Homo sapiens
<220> FEATURE:
<221> NAME/KEY: CDS
<222> LOCATION: (1)..(939)

<400> SEQUENCE: 9 atg gat gga ggc aac cag agt gaa ggt tca gag ttc ctt ctc ctg ggg      48
Met Asp Gly Gly Asn Gln Ser Glu Gly Ser Glu Phe Leu Leu Leu Gly
1               5                   10                  15 atg tca gag agt cct gag cag cag cgg atc ctg ttt tgg atg ttc ctg      96
Met Ser Glu Ser Pro Glu Gln Gln Arg Ile Leu Phe Trp Met Phe Leu
            20                  25                  30 tcc atg tac ctg gtc acg gtg gtg gga aat gtg ctc atc atc ctg gcc     144
Ser Met Tyr Leu Val Thr Val Val Gly Asn Val Leu Ile Ile Leu Ala
        35                  40                  45 atc agc tct gat tcc cgc ctg cac acc ccc gtg tac ttc ttc ctg gcc     192
Ile Ser Ser Asp Ser Arg Leu His Thr Pro Val Tyr Phe Phe Leu Ala
    50                  55                  60 aac ctc tcc ttc act gac ctc ttc ttt gtc acc aac aca atc ccc aag     240
Asn Leu Ser Phe Thr Asp Leu Phe Phe Val Thr Asn Thr Ile Pro Lys
65                  70                  75                  80 atg ctg gtg aac ctc cag tcc cat aac aaa gcc atc tcc tat gca ggg     288
Met Leu Val Asn Leu Gln Ser His Asn Lys Ala Ile Ser Tyr Ala Gly
                85                  90                  95 tgt ctg aca cag ctc tac ttc ctg gtc tcc ttg gtg gcc ctg gac aac     336
Cys Leu Thr Gln Leu Tyr Phe Leu Val Ser Leu Val Ala Leu Asp Asn
```

```
ctc atc ctg gct gtg atg gca tat gac cgc tat gtg gcc atc tgc tgc    384
Leu Ile Leu Ala Val Met Ala Tyr Asp Arg Tyr Val Ala Ile Cys Cys
            115                 120                 125 ccc ctc cac tac acc aca gcc atg agc cct aag ctc tgt atc tta ctc    432
Pro Leu His Tyr Thr Thr Ala Met Ser Pro Lys Leu Cys Ile Leu Leu
130                 135                 140 ctt tcc ttg tgt tgg gtc cta tcc gtc ctc tat ggc ctc ata cac acc    480
Leu Ser Leu Cys Trp Val Leu Ser Val Leu Tyr Gly Leu Ile His Thr
145                 150                 155                 160 ctc ctc atg acc aga gtg acc ttc tgt ggg tca cga aaa atc cac tac    528
Leu Leu Met Thr Arg Val Thr Phe Cys Gly Ser Arg Lys Ile His Tyr
                165                 170                 175 atc ttc tgt gag atg tat gta ttg ctg agg atg gca tgt tcc aac att    576
Ile Phe Cys Glu Met Tyr Val Leu Leu Arg Met Ala Cys Ser Asn Ile
            180                 185                 190 cag att aat cac aca gtg ctg att gcc aca ggc tgc ttc atc ttc ctc    624
Gln Ile Asn His Thr Val Leu Ile Ala Thr Gly Cys Phe Ile Phe Leu
        195                 200                 205 att ccc ttt gga ttc gtg atc att tcc tat gtg ctg att atc aga gcc    672
Ile Pro Phe Gly Phe Val Ile Ile Ser Tyr Val Leu Ile Ile Arg Ala
210                 215                 220 atc ctc aga ata ccc tca gtc tct aag aaa tac aaa gcc ttc tcc acc    720
Ile Leu Arg Ile Pro Ser Val Ser Lys Lys Tyr Lys Ala Phe Ser Thr
225                 230                 235                 240 tgt gcc tcc cat ttg ggt gca gtc tcc ctc ttc tat ggg aca ctt tgt    768
Cys Ala Ser His Leu Gly Ala Val Ser Leu Phe Tyr Gly Thr Leu Cys
                245                 250                 255 atg gta tac cta aag ccc ctc cat acc tac tct gtg aag gac tca gta    816
Met Val Tyr Leu Lys Pro Leu His Thr Tyr Ser Val Lys Asp Ser Val
            260                 265                 270 gcc aca gtg atg tat gct gtg gtg aca ccc atg atg aat ccc ttc atc    864
Ala Thr Val Met Tyr Ala Val Val Thr Pro Met Met Asn Pro Phe Ile
        275                 280                 285 tac agc ctg agg aac aag gac atg cat ggg gct ctg gga aga ctc cta    912
Tyr Ser Leu Arg Asn Lys Asp Met His Gly Ala Leu Gly Arg Leu Leu
290                 295                 300 gat aaa cac ttt aag agg ctg aca tga                                939
Asp Lys His Phe Lys Arg Leu Thr
305                 310

<210> SEQ ID NO 10
<211> LENGTH: 312
<212> TYPE: PRT
<213> ORGANISM: Homo sapiens

<400> SEQUENCE: 10

Met Asp Gly Gly Asn Gln Ser Glu Gly Ser Glu Phe Leu Leu Leu Gly
1               5                   10                  15

Met Ser Glu Ser Pro Glu Gln Gln Arg Ile Leu Phe Trp Met Phe Leu
            20                  25                  30

Ser Met Tyr Leu Val Thr Val Val Gly Asn Val Leu Ile Ile Leu Ala
        35                  40                  45

Ile Ser Ser Asp Ser Arg Leu His Thr Pro Val Tyr Phe Phe Leu Ala
    50                  55                  60

Asn Leu Ser Phe Thr Asp Leu Phe Phe Val Thr Asn Thr Ile Pro Lys
65                  70                  75                  80

Met Leu Val Asn Leu Gln Ser His Asn Lys Ala Ile Ser Tyr Ala Gly
                85                  90                  95
```

```
Cys Leu Thr Gln Leu Tyr Phe Leu Val Ser Leu Val Ala Leu Asp Asn
                100                 105                 110

Leu Ile Leu Ala Val Met Ala Tyr Asp Arg Tyr Val Ala Ile Cys Cys
            115                 120                 125

Pro Leu His Tyr Thr Thr Ala Met Ser Pro Lys Leu Cys Ile Leu Leu
        130                 135                 140

Leu Ser Leu Cys Trp Val Leu Ser Val Leu Tyr Gly Leu Ile His Thr
145                 150                 155                 160

Leu Leu Met Thr Arg Val Thr Phe Cys Gly Ser Arg Lys Ile His Tyr
                165                 170                 175

Ile Phe Cys Glu Met Tyr Val Leu Leu Arg Met Ala Cys Ser Asn Ile
            180                 185                 190

Gln Ile Asn His Thr Val Leu Ile Ala Thr Gly Cys Phe Ile Phe Leu
        195                 200                 205

Ile Pro Phe Gly Phe Val Ile Ile Ser Tyr Val Leu Ile Ile Arg Ala
210                 215                 220

Ile Leu Arg Ile Pro Ser Val Ser Lys Lys Tyr Lys Ala Phe Ser Thr
225                 230                 235                 240

Cys Ala Ser His Leu Gly Ala Val Ser Leu Phe Tyr Gly Thr Leu Cys
                245                 250                 255

Met Val Tyr Leu Lys Pro Leu His Thr Tyr Ser Val Lys Asp Ser Val
            260                 265                 270

Ala Thr Val Met Tyr Ala Val Val Thr Pro Met Met Asn Pro Phe Ile
        275                 280                 285

Tyr Ser Leu Arg Asn Lys Asp Met His Gly Ala Leu Gly Arg Leu Leu
        290                 295                 300

Asp Lys His Phe Lys Arg Leu Thr
305                 310

<210> SEQ ID NO 11
<211> LENGTH: 966
<212> TYPE: DNA
<213> ORGANISM: Homo sapiens
<220> FEATURE:
<221> NAME/KEY: CDS
<222> LOCATION: (1)..(966)

<400> SEQUENCE: 11 atg tct ggg gac aac agc tcc agc ctg acc cca gga ttc ttt atc ttg        48
Met Ser Gly Asp Asn Ser Ser Ser Leu Thr Pro Gly Phe Phe Ile Leu
1               5                   10                  15 aat ggc gtt cct ggg ctg gaa gcc aca cac atc tgg atc tcc ctg cca        96
Asn Gly Val Pro Gly Leu Glu Ala Thr His Ile Trp Ile Ser Leu Pro
            20                  25                  30 ttc tgc ttt atg tac atc att gct gtc gtg ggg aac tgt ggg ctc atc       144
Phe Cys Phe Met Tyr Ile Ile Ala Val Val Gly Asn Cys Gly Leu Ile
        35                  40                  45 tgc ctc atc agc cat gag gag gcc ctg cac cgg ccc atg tac tac ttc       192
Cys Leu Ile Ser His Glu Glu Ala Leu His Arg Pro Met Tyr Tyr Phe
    50                  55                  60 ctg gcc ctg ctc tcc ttc act gat gtc acc ttg tgc acc acc atg gta       240
Leu Ala Leu Leu Ser Phe Thr Asp Val Thr Leu Cys Thr Thr Met Val
65                  70                  75                  80 cct aat atg ctg tgc ata ttc tgg ttc aac ctc aag gag att gac ttt       288
Pro Asn Met Leu Cys Ile Phe Trp Phe Asn Leu Lys Glu Ile Asp Phe
                85                  90                  95 aac gcc tgc ctg gcc cag atg ttt ttt gtc cat atg ctg aca ggg atg       336
```

```
                Asn Ala Cys Leu Ala Gln Met Phe Phe Val His Met Leu Thr Gly Met
                                100                 105                 110 gag tct ggg gtg ctc atg ctc atg gcc ctg gac cgc tat gtg gcc atc        384
Glu Ser Gly Val Leu Met Leu Met Ala Leu Asp Arg Tyr Val Ala Ile
            115                 120                 125 tgc tac ccc tta cgc tat gcc acc atc ctt acc aac cct gtc atc gcc        432
Cys Tyr Pro Leu Arg Tyr Ala Thr Ile Leu Thr Asn Pro Val Ile Ala
130                 135                 140 aag gct ggt ctt gcc acc ttc ttg agg aat gtg atg ctc atc atc cca        480
Lys Ala Gly Leu Ala Thr Phe Leu Arg Asn Val Met Leu Ile Ile Pro
145                 150                 155                 160 ttc act ctc ctc acc aag cgc ctg ccc tat tgc cgg ggg aac ttc atc        528
Phe Thr Leu Leu Thr Lys Arg Leu Pro Tyr Cys Arg Gly Asn Phe Ile
                165                 170                 175 ccc cac acc tac tgt gac cat atg tct gtg gcc aag gta tcc tgt ggc        576
Pro His Thr Tyr Cys Asp His Met Ser Val Ala Lys Val Ser Cys Gly
            180                 185                 190 aat ttc aag gtc aat gct att tat ggt ctg atg gtt gct ctc ctg att        624
Asn Phe Lys Val Asn Ala Ile Tyr Gly Leu Met Val Ala Leu Leu Ile
        195                 200                 205 ggt gtg ttt gat atc tgc tgt atc tct gta tct tac act atg att ttg        672
Gly Val Phe Asp Ile Cys Cys Ile Ser Val Ser Tyr Thr Met Ile Leu
210                 215                 220 cag gct gtt atg agc ctg tca tca gca gat gct cgt cac aaa gcc ttc        720
Gln Ala Val Met Ser Leu Ser Ser Ala Asp Ala Arg His Lys Ala Phe
225                 230                 235                 240 agc acc tgc aca tct cac atg tgt tcc att gtg atc acc tat gtt gct        768
Ser Thr Cys Thr Ser His Met Cys Ser Ile Val Ile Thr Tyr Val Ala
                245                 250                 255 gct ttt ttc act ttt ttc act cat cgt ttt gta gga cac aat atc cca        816
Ala Phe Phe Thr Phe Phe Thr His Arg Phe Val Gly His Asn Ile Pro
            260                 265                 270 aac cac ata cac atc atc gtg gcc aac ctt tat ctg cta ctg cct cct        864
Asn His Ile His Ile Ile Val Ala Asn Leu Tyr Leu Leu Leu Pro Pro
        275                 280                 285 acc atg aac cca att gtt tat gga gtc aag acc aag cag att cag gaa        912
Thr Met Asn Pro Ile Val Tyr Gly Val Lys Thr Lys Gln Ile Gln Glu
290                 295                 300 ggt gta att aaa ttt tta ctt gga gac aag gtt agt ttt acc tat gac        960
Gly Val Ile Lys Phe Leu Leu Gly Asp Lys Val Ser Phe Thr Tyr Asp
305                 310                 315                 320 aaa tga                                                                966
Lys

<210> SEQ ID NO 12
<211> LENGTH: 321
<212> TYPE: PRT
<213> ORGANISM: Homo sapiens

<400> SEQUENCE: 12

Met Ser Gly Asp Asn Ser Ser Leu Thr Pro Gly Phe Phe Ile Leu
1               5                   10                  15

Asn Gly Val Pro Gly Leu Glu Ala Thr His Ile Trp Ile Ser Leu Pro
                20                  25                  30

Phe Cys Phe Met Tyr Ile Ile Ala Val Val Gly Asn Cys Gly Leu Ile
            35                  40                  45

Cys Leu Ile Ser His Glu Glu Ala Leu His Arg Pro Met Tyr Tyr Phe
        50                  55                  60

Leu Ala Leu Leu Ser Phe Thr Asp Val Thr Leu Cys Thr Thr Met Val
```

```
                65                    70                    75                    80
Pro Asn Met Leu Cys Ile Phe Trp Phe Asn Leu Lys Glu Ile Asp Phe
                        85                    90                    95

Asn Ala Cys Leu Ala Gln Met Phe Phe Val His Met Leu Thr Gly Met
            100                       105                   110

Glu Ser Gly Val Leu Met Leu Met Ala Leu Asp Arg Tyr Val Ala Ile
        115                       120                   125

Cys Tyr Pro Leu Arg Tyr Ala Thr Ile Leu Thr Asn Pro Val Ile Ala
    130                       135                   140

Lys Ala Gly Leu Ala Thr Phe Leu Arg Asn Val Met Leu Ile Ile Pro
145                     150                   155                   160

Phe Thr Leu Leu Thr Lys Arg Leu Pro Tyr Cys Arg Gly Asn Phe Ile
                    165                   170                   175

Pro His Thr Tyr Cys Asp His Met Ser Val Ala Lys Val Ser Cys Gly
                180                   185                   190

Asn Phe Lys Val Asn Ala Ile Tyr Gly Leu Met Val Ala Leu Leu Ile
            195                   200                   205

Gly Val Phe Asp Ile Cys Cys Ile Ser Val Ser Tyr Thr Met Ile Leu
        210                   215                   220

Gln Ala Val Met Ser Leu Ser Ser Ala Asp Ala Arg His Lys Ala Phe
225                   230                   235                   240

Ser Thr Cys Thr Ser His Met Cys Ser Ile Val Ile Thr Tyr Val Ala
                    245                   250                   255

Ala Phe Phe Thr Phe Phe Thr His Arg Phe Val Gly His Asn Ile Pro
                260                   265                   270

Asn His Ile His Ile Ile Val Ala Asn Leu Tyr Leu Leu Leu Pro Pro
            275                   280                   285

Thr Met Asn Pro Ile Val Tyr Gly Val Lys Thr Lys Gln Ile Gln Glu
        290                   295                   300

Gly Val Ile Lys Phe Leu Leu Gly Asp Lys Val Ser Phe Thr Tyr Asp
305                   310                   315                   320

Lys

<210> SEQ ID NO 13
<211> LENGTH: 1075
<212> TYPE: DNA
<213> ORGANISM: Homo sapiens
<220> FEATURE:
<221> NAME/KEY: CDS
<222> LOCATION: (82)..(1017)

<400> SEQUENCE: 13
catgtgtgct gatattttg gatcatttgt ttactcgttt tttgagttta cctttctttt      60
ttttctctca ggtaatagga a atg aat gat gat gga aaa gtc aat gct agc     111
                        Met Asn Asp Asp Gly Lys Val Asn Ala Ser
                          1               5                  10 tct gag ggg tac ttt att tta gtt gga ttt tct aat tgg cct cat ctg     159
Ser Glu Gly Tyr Phe Ile Leu Val Gly Phe Ser Asn Trp Pro His Leu
                15                  20                  25 gaa gta gtt atc ttt gtg gtt gtc ttg atc ttc tac ttg atg aca ctg     207
Glu Val Val Ile Phe Val Val Val Leu Ile Phe Tyr Leu Met Thr Leu
            30                  35                  40 ata gga aac ctg ttc atc atc atc ctg tca tac ctg gac tcc cat ctg     255
Ile Gly Asn Leu Phe Ile Ile Ile Leu Ser Tyr Leu Asp Ser His Leu
        45                  50                  55 cac aca cca atg tac ttc ttc ctt tca aac ctc tca ttt ctg gat ctc     303
```

```
                His Thr Pro Met Tyr Phe Phe Leu Ser Asn Leu Ser Phe Leu Asp Leu
                    60                  65                  70 tgc tac acc acc agc tct atc cct cag ttg ctg gtc aat ctc tgg ggc        351
Cys Tyr Thr Thr Ser Ser Ile Pro Gln Leu Leu Val Asn Leu Trp Gly
 75                  80                  85                  90 ccg gaa aag acc atc tct tat gct ggt tgc atg att caa ctt tac ttt        399
Pro Glu Lys Thr Ile Ser Tyr Ala Gly Cys Met Ile Gln Leu Tyr Phe
                     95                 100                 105 gtt ctc gca ctg gga acc aca gag tgt gtc cta ctg gtg gtg atg tcc        447
Val Leu Ala Leu Gly Thr Thr Glu Cys Val Leu Leu Val Val Met Ser
                110                 115                 120 tat gac cgt tat gca gct gtg tgt aga cct ttg cat tac act gtc ctc        495
Tyr Asp Arg Tyr Ala Ala Val Cys Arg Pro Leu His Tyr Thr Val Leu
            125                 130                 135 atg cac cct cgt ttc tgc cac ctg ctg gct gtg gct tct tgg gta agt        543
Met His Pro Arg Phe Cys His Leu Leu Ala Val Ala Ser Trp Val Ser
            140                 145                 150 ggt ttt acc aac tca gca ctt cat tcc tcc ttc acc ttc tgg gta cct        591
Gly Phe Thr Asn Ser Ala Leu His Ser Ser Phe Thr Phe Trp Val Pro
155                 160                 165                 170 ctg tgt gga cac cgc caa gta gat cac ttt ttc tgt gaa gtt cca gca        639
Leu Cys Gly His Arg Gln Val Asp His Phe Phe Cys Glu Val Pro Ala
                175                 180                 185 ctt ctg cga tta tcg tgt gtt gat acc cat gtc aat gag ctg acc ctc        687
Leu Leu Arg Leu Ser Cys Val Asp Thr His Val Asn Glu Leu Thr Leu
                190                 195                 200 atg atc aca agc tcc ata ttt gtt ctc ata cct ctc atc ctc att ctc        735
Met Ile Thr Ser Ser Ile Phe Val Leu Ile Pro Leu Ile Leu Ile Leu
            205                 210                 215 act tct tat ggt gcc atc gtc cga gct ata ctg agg atg cag tca acc        783
Thr Ser Tyr Gly Ala Ile Val Arg Ala Ile Leu Arg Met Gln Ser Thr
            220                 225                 230 act ggg ctt cag aaa gtg ttt gga aca tgt gga gct cat ctt atg gct        831
Thr Gly Leu Gln Lys Val Phe Gly Thr Cys Gly Ala His Leu Met Ala
235                 240                 245                 250 gta tct ctc ttt ttc att ccg gcc atg tgc atg tat ctc cag cca cca        879
Val Ser Leu Phe Phe Ile Pro Ala Met Cys Met Tyr Leu Gln Pro Pro
                255                 260                 265 tca gga aat tct caa gat caa ggc aag ttc att gcc ctc ttt tat act        927
Ser Gly Asn Ser Gln Asp Gln Gly Lys Phe Ile Ala Leu Phe Tyr Thr
                270                 275                 280 gtt gtc aca cct agt ctt aac cct cta atc tac acc ctc aga aac aaa        975
Val Val Thr Pro Ser Leu Asn Pro Leu Ile Tyr Thr Leu Arg Asn Lys
            285                 290                 295 gtt gta aga ggg gca gtg aag aga cta atg ggg tgg gaa tga               1017
Val Val Arg Gly Ala Val Lys Arg Leu Met Gly Trp Glu
300                 305                 310 gcctgtgtat gtgtcatatt aacaatataa cagagtctcc cctcacaatg attcatcc       1075

<210> SEQ ID NO 14
<211> LENGTH: 311
<212> TYPE: PRT
<213> ORGANISM: Homo sapiens

<400> SEQUENCE: 14

Met Asn Asp Asp Gly Lys Val Asn Ala Ser Ser Glu Gly Tyr Phe Ile
1               5                   10                  15

Leu Val Gly Phe Ser Asn Trp Pro His Leu Glu Val Val Ile Phe Val
            20                  25                  30
```

```
Val Val Leu Ile Phe Tyr Leu Met Thr Leu Ile Gly Asn Leu Phe Ile
         35                  40                  45

Ile Ile Leu Ser Tyr Leu Asp Ser His Leu His Thr Pro Met Tyr Phe
 50                  55                  60

Phe Leu Ser Asn Leu Ser Phe Leu Asp Leu Cys Tyr Thr Thr Ser Ser
 65                  70                  75                  80

Ile Pro Gln Leu Leu Val Asn Leu Trp Gly Pro Glu Lys Thr Ile Ser
                 85                  90                  95

Tyr Ala Gly Cys Met Ile Gln Leu Tyr Phe Val Leu Ala Leu Gly Thr
            100                 105                 110

Thr Glu Cys Val Leu Leu Val Val Met Ser Tyr Asp Arg Tyr Ala Ala
        115                 120                 125

Val Cys Arg Pro Leu His Tyr Thr Val Leu Met His Pro Arg Phe Cys
130                 135                 140

His Leu Leu Ala Val Ala Ser Trp Val Ser Gly Phe Thr Asn Ser Ala
145                 150                 155                 160

Leu His Ser Ser Phe Thr Phe Trp Val Pro Leu Cys Gly His Arg Gln
                165                 170                 175

Val Asp His Phe Phe Cys Glu Val Pro Ala Leu Leu Arg Leu Ser Cys
            180                 185                 190

Val Asp Thr His Val Asn Glu Leu Thr Leu Met Ile Thr Ser Ser Ile
        195                 200                 205

Phe Val Leu Ile Pro Leu Ile Leu Ile Leu Thr Ser Tyr Gly Ala Ile
210                 215                 220

Val Arg Ala Ile Leu Arg Met Gln Ser Thr Thr Gly Leu Gln Lys Val
225                 230                 235                 240

Phe Gly Thr Cys Gly Ala His Leu Met Ala Val Ser Leu Phe Phe Ile
                245                 250                 255

Pro Ala Met Cys Met Tyr Leu Gln Pro Pro Ser Gly Asn Ser Gln Asp
            260                 265                 270

Gln Gly Lys Phe Ile Ala Leu Phe Tyr Thr Val Val Thr Pro Ser Leu
        275                 280                 285

Asn Pro Leu Ile Tyr Thr Leu Arg Asn Lys Val Val Arg Gly Ala Val
290                 295                 300

Lys Arg Leu Met Gly Trp Glu
305                 310

<210> SEQ ID NO 15
<211> LENGTH: 936
<212> TYPE: DNA
<213> ORGANISM: Homo sapiens
<220> FEATURE:
<221> NAME/KEY: CDS
<222> LOCATION: (1)..(936)

<400> SEQUENCE: 15 atg gga ccc aga aac caa aca gct gtt tca gaa ttt ctt ctc atg aaa    48
Met Gly Pro Arg Asn Gln Thr Ala Val Ser Glu Phe Leu Leu Met Lys
 1               5                  10                  15 gtg aca gag gac cca gaa ctg aag tta atc cct ttc agc ctg ttc ctg    96
Val Thr Glu Asp Pro Glu Leu Lys Leu Ile Pro Phe Ser Leu Phe Leu
             20                  25                  30 tcc atg tac ctg gtc acc atc ctg ggg aac ctg ctc att ctc tgg gct   144
Ser Met Tyr Leu Val Thr Ile Leu Gly Asn Leu Leu Ile Leu Leu Ala
         35                  40                  45 gtc atc tct gac tcc cac ctc cac acc ccc atg tac ttc ctt ctc ttt   192
Val Ile Ser Asp Ser His Leu His Thr Pro Met Tyr Phe Leu Leu Phe
```

```
aat ctc tcc ttt act gac atc tgt tta acc aca acc aca gtc cca aag      240
Asn Leu Ser Phe Thr Asp Ile Cys Leu Thr Thr Thr Thr Val Pro Lys
 65                  70                  75                  80 atc cta gtg aac atc caa gct cag aat cag agt atc act tac aca ggc      288
Ile Leu Val Asn Ile Gln Ala Gln Asn Gln Ser Ile Thr Tyr Thr Gly
                 85                  90                  95 tgc ctc acc cag atc tgt ctt gtc ttg gtt ttt gct ggc ttg gaa agt      336
Cys Leu Thr Gln Ile Cys Leu Val Leu Val Phe Ala Gly Leu Glu Ser
            100                 105                 110 tgc ttt ctt gca gtc atg gcc tac gac cgc tat gtg gcc att tgc cac      384
Cys Phe Leu Ala Val Met Ala Tyr Asp Arg Tyr Val Ala Ile Cys His
        115                 120                 125 cca ctg agg tac aca gtc ctc atg aat gtc cat ttc tgg ggc ttg ctg      432
Pro Leu Arg Tyr Thr Val Leu Met Asn Val His Phe Trp Gly Leu Leu
    130                 135                 140 att ctt ctc tcc atg ttc atg agc act atg gat gcc ctg gtt cag agt      480
Ile Leu Leu Ser Met Phe Met Ser Thr Met Asp Ala Leu Val Gln Ser
145                 150                 155                 160 ctg atg gta ttg cag ctg tcc ttc tgc aaa aac gtt gaa atc cct ttg      528
Leu Met Val Leu Gln Leu Ser Phe Cys Lys Asn Val Glu Ile Pro Leu
                165                 170                 175 ttc ttc tgt gaa gtc gtt cag gtc atc aag ctc gcc tgt tct gac acc      576
Phe Phe Cys Glu Val Val Gln Val Ile Lys Leu Ala Cys Ser Asp Thr
            180                 185                 190 ctc atc aac aac atc ctc ata tat ttt gca agt agt gta ttt ggt gca      624
Leu Ile Asn Asn Ile Leu Ile Tyr Phe Ala Ser Ser Val Phe Gly Ala
        195                 200                 205 att cct ctc tct gga ata att ttc tct tat tct caa ata gtc acc tct      672
Ile Pro Leu Ser Gly Ile Ile Phe Ser Tyr Ser Gln Ile Val Thr Ser
    210                 215                 220 gtt ctg aga atg cca tca gca aga gga aag tat aaa gcg ttt tcc acc      720
Val Leu Arg Met Pro Ser Ala Arg Gly Lys Tyr Lys Ala Phe Ser Thr
225                 230                 235                 240 tgt ggc tgt cac ctc tct gtt ttt tcc ttg ttc tat ggg aca gct ttt      768
Cys Gly Cys His Leu Ser Val Phe Ser Leu Phe Tyr Gly Thr Ala Phe
                245                 250                 255 ggg gtg tac att agt tct gct gtt gct gag tct tcc cga att act gct      816
Gly Val Tyr Ile Ser Ser Ala Val Ala Glu Ser Ser Arg Ile Thr Ala
            260                 265                 270 gtg gct tca gtg atg tac act gtg gtc cct caa atg atg aac ccc ttc      864
Val Ala Ser Val Met Tyr Thr Val Val Pro Gln Met Met Asn Pro Phe
        275                 280                 285 atc tac agc ctg aga aat aag gag atg aag aaa gct ttg agg aaa ctt      912
Ile Tyr Ser Leu Arg Asn Lys Glu Met Lys Lys Ala Leu Arg Lys Leu
    290                 295                 300 att ggt agg ctg ttt cct ttt tag                                      936
Ile Gly Arg Leu Phe Pro Phe
305                 310

<210> SEQ ID NO 16
<211> LENGTH: 311
<212> TYPE: PRT
<213> ORGANISM: Homo sapiens

<400> SEQUENCE: 16

Met Gly Pro Arg Asn Gln Thr Ala Val Ser Glu Phe Leu Leu Met Lys
1               5                   10                  15

Val Thr Glu Asp Pro Glu Leu Lys Leu Ile Pro Phe Ser Leu Phe Leu
            20                  25                  30
```

```
Ser Met Tyr Leu Val Thr Ile Leu Gly Asn Leu Leu Ile Leu Leu Ala
        35                  40                  45

Val Ile Ser Asp Ser His Leu His Thr Pro Met Tyr Phe Leu Leu Phe
 50                  55                  60

Asn Leu Ser Phe Thr Asp Ile Cys Leu Thr Thr Thr Val Pro Lys
65                  70                  75                  80

Ile Leu Val Asn Ile Gln Ala Gln Asn Gln Ser Ile Thr Tyr Thr Gly
                85                  90                  95

Cys Leu Thr Gln Ile Cys Leu Val Leu Val Phe Ala Gly Leu Glu Ser
                100                 105                 110

Cys Phe Leu Ala Val Met Ala Tyr Asp Arg Tyr Val Ala Ile Cys His
                115                 120                 125

Pro Leu Arg Tyr Thr Val Leu Met Asn Val His Phe Trp Gly Leu Leu
        130                 135                 140

Ile Leu Leu Ser Met Phe Met Ser Thr Met Asp Ala Leu Val Gln Ser
145                 150                 155                 160

Leu Met Val Leu Gln Leu Ser Phe Cys Lys Asn Val Glu Ile Pro Leu
                165                 170                 175

Phe Phe Cys Glu Val Val Gln Val Ile Lys Leu Ala Cys Ser Asp Thr
                180                 185                 190

Leu Ile Asn Asn Ile Leu Ile Tyr Phe Ala Ser Ser Val Phe Gly Ala
        195                 200                 205

Ile Pro Leu Ser Gly Ile Ile Phe Ser Tyr Ser Gln Ile Val Thr Ser
        210                 215                 220

Val Leu Arg Met Pro Ser Ala Arg Gly Lys Tyr Lys Ala Phe Ser Thr
225                 230                 235                 240

Cys Gly Cys His Leu Ser Val Phe Ser Leu Phe Tyr Gly Thr Ala Phe
                245                 250                 255

Gly Val Tyr Ile Ser Ser Ala Val Ala Glu Ser Ser Arg Ile Thr Ala
                260                 265                 270

Val Ala Ser Val Met Tyr Thr Val Val Pro Gln Met Met Asn Pro Phe
        275                 280                 285

Ile Tyr Ser Leu Arg Asn Lys Glu Met Lys Lys Ala Leu Arg Lys Leu
        290                 295                 300

Ile Gly Arg Leu Phe Pro Phe
305                 310

<210> SEQ ID NO 17
<211> LENGTH: 945
<212> TYPE: DNA
<213> ORGANISM: Homo sapiens
<220> FEATURE:
<221> NAME/KEY: CDS
<222> LOCATION: (1)..(945)

<400> SEQUENCE: 17 atg gcc aag aat aat ctc acc aga gta acc gaa ttc att ctc atg ggc        48
Met Ala Lys Asn Asn Leu Thr Arg Val Thr Glu Phe Ile Leu Met Gly
 1               5                  10                  15 ttt atg gac cac ccc aaa ttg gag att ccc ctc ttt ctg gtg ttt ctg        96
Phe Met Asp His Pro Lys Leu Glu Ile Pro Leu Phe Leu Val Phe Leu
                20                  25                  30 agt ttc tac cta gtc acc ctt ctt ggg aat gtg ggg atg att atg tta       144
Ser Phe Tyr Leu Val Thr Leu Leu Gly Asn Val Gly Met Ile Met Leu
        35                  40                  45 atc caa gta gat gtc aaa ctc tac acc cca atg tac ttc ttc ctg agc       192
```

```
              Ile Gln Val Asp Val Lys Leu Tyr Thr Pro Met Tyr Phe Phe Leu Ser
                  50                  55                  60 cac ctc tcc ctg ctg gat gcc tgt tac acc tca gtc atc acc cct cag        240
His Leu Ser Leu Leu Asp Ala Cys Tyr Thr Ser Val Ile Thr Pro Gln
 65                  70                  75                  80 atc cta gcc aca ttg gcc aca ggc aaa acg gtc atc tcc tac ggc cac        288
Ile Leu Ala Thr Leu Ala Thr Gly Lys Thr Val Ile Ser Tyr Gly His
                 85                  90                  95 tgt gct gcc cag ttc ttt tta ttc acc atc tgt gca ggc aca gag tgc        336
Cys Ala Ala Gln Phe Phe Leu Phe Thr Ile Cys Ala Gly Thr Glu Cys
            100                 105                 110 ttt ctg ctg gca gtg atg gcc tat gat cgc tat gct gcc att cgc aac        384
Phe Leu Leu Ala Val Met Ala Tyr Asp Arg Tyr Ala Ala Ile Arg Asn
        115                 120                 125 cca ctg ctc tat acc gtg gcc atg aat ccc agg ctc tgc tgg agc ctg        432
Pro Leu Leu Tyr Thr Val Ala Met Asn Pro Arg Leu Cys Trp Ser Leu
    130                 135                 140 gta gga gcc tat gtc tgt ggg gtg tca gga gcc atc ctg cgt acc            480
Val Val Gly Ala Tyr Val Cys Gly Val Ser Gly Ala Ile Leu Arg Thr
145                 150                 155                 160 act tgc acc ttc acc ctc tcc ttc tgt aag gac aat caa ata aac ttc        528
Thr Cys Thr Phe Thr Leu Ser Phe Cys Lys Asp Asn Gln Ile Asn Phe
                165                 170                 175 ttc ttc tgt gac ctc cca ccc ctg ctg aag ctt gcc tgc agt gac aca        576
Phe Phe Cys Asp Leu Pro Pro Leu Leu Lys Leu Ala Cys Ser Asp Thr
            180                 185                 190 gca aac atc gag att gtc atc atc ttc ttt ggc aat ttt gtg att ttg        624
Ala Asn Ile Glu Ile Val Ile Ile Phe Phe Gly Asn Phe Val Ile Leu
        195                 200                 205 gcc aat gcc tcc gtc atc ctg att tcc tat ctg ctc atc atc aag acc        672
Ala Asn Ala Ser Val Ile Leu Ile Ser Tyr Leu Leu Ile Ile Lys Thr
    210                 215                 220 att ttg aaa gtg aag tct tca ggt ggc agg gcc aag act ttc tcc aca        720
Ile Leu Lys Val Lys Ser Ser Gly Gly Arg Ala Lys Thr Phe Ser Thr
225                 230                 235                 240 tgt gcc tct cac atc act gct gtg gcc ctt ttc ttt gga gcc ctt atc        768
Cys Ala Ser His Ile Thr Ala Val Ala Leu Phe Phe Gly Ala Leu Ile
                245                 250                 255 ttc atg tat ctg caa agt ggc tca ggc aaa tct ctg gag gaa gac aaa        816
Phe Met Tyr Leu Gln Ser Gly Ser Gly Lys Ser Leu Glu Glu Asp Lys
            260                 265                 270 gtc gtg tct gtc ttc tat aca gtg gtc atc ccc atg ctg aac cct ctg        864
Val Val Ser Val Phe Tyr Thr Val Val Ile Pro Met Leu Asn Pro Leu
        275                 280                 285 atc tac agc tta aga aac aaa gat gta aaa gac gcc ttc aga aag gtc        912
Ile Tyr Ser Leu Arg Asn Lys Asp Val Lys Asp Ala Phe Arg Lys Val
    290                 295                 300 gct agg aga ctc cag gtg tcc ctg agc atg tag                            945
Ala Arg Arg Leu Gln Val Ser Leu Ser Met
305                 310

<210> SEQ ID NO 18
<211> LENGTH: 314
<212> TYPE: PRT
<213> ORGANISM: Homo sapiens

<400> SEQUENCE: 18

Met Ala Lys Asn Asn Leu Thr Arg Val Thr Glu Phe Ile Leu Met Gly
 1               5                  10                  15

Phe Met Asp His Pro Lys Leu Glu Ile Pro Leu Phe Leu Val Phe Leu
```

```
                 20                  25                  30
Ser Phe Tyr Leu Val Thr Leu Leu Gly Asn Val Gly Met Ile Met Leu
             35                  40                  45

Ile Gln Val Asp Val Lys Leu Tyr Thr Pro Met Tyr Phe Phe Leu Ser
 50                  55                  60

His Leu Ser Leu Leu Asp Ala Cys Tyr Thr Ser Val Ile Thr Pro Gln
 65                  70                  75                  80

Ile Leu Ala Thr Leu Ala Thr Gly Lys Thr Val Ile Ser Tyr Gly His
             85                  90                  95

Cys Ala Ala Gln Phe Phe Leu Phe Thr Ile Cys Ala Gly Thr Glu Cys
            100                 105                 110

Phe Leu Leu Ala Val Met Ala Tyr Asp Arg Tyr Ala Ala Ile Arg Asn
            115                 120                 125

Pro Leu Leu Tyr Thr Val Ala Met Asn Pro Arg Leu Cys Trp Ser Leu
            130                 135                 140

Val Val Gly Ala Tyr Val Cys Gly Val Ser Gly Ala Ile Leu Arg Thr
145                 150                 155                 160

Thr Cys Thr Phe Thr Leu Ser Phe Cys Lys Asp Asn Gln Ile Asn Phe
                165                 170                 175

Phe Phe Cys Asp Leu Pro Pro Leu Leu Lys Leu Ala Cys Ser Asp Thr
            180                 185                 190

Ala Asn Ile Glu Ile Val Ile Phe Phe Gly Asn Phe Val Ile Leu
            195                 200                 205

Ala Asn Ala Ser Val Ile Leu Ile Ser Tyr Leu Leu Ile Ile Lys Thr
            210                 215                 220

Ile Leu Lys Val Lys Ser Ser Gly Arg Ala Lys Thr Phe Ser Thr
225                 230                 235                 240

Cys Ala Ser His Ile Thr Ala Val Ala Leu Phe Phe Gly Ala Leu Ile
                245                 250                 255

Phe Met Tyr Leu Gln Ser Gly Ser Gly Lys Ser Leu Glu Glu Asp Lys
            260                 265                 270

Val Val Ser Val Phe Tyr Thr Val Val Ile Pro Met Leu Asn Pro Leu
            275                 280                 285

Ile Tyr Ser Leu Arg Asn Lys Asp Val Lys Asp Ala Phe Arg Lys Val
            290                 295                 300

Ala Arg Arg Leu Gln Val Ser Leu Ser Met
305                 310

<210> SEQ ID NO 19
<211> LENGTH: 939
<212> TYPE: DNA
<213> ORGANISM: Homo sapiens
<220> FEATURE:
<221> NAME/KEY: CDS
<222> LOCATION: (1)..(939)

<400> SEQUENCE: 19 atg tct gtt ctc aat aac tcc gaa gtc aag ctt ttc ctt ctg att ggg    48
Met Ser Val Leu Asn Asn Ser Glu Val Lys Leu Phe Leu Leu Ile Gly
 1               5                  10                  15 atc cca gga ctg gaa cat gcc cac att tgg ttc tcc atc ccc att tgc    96
Ile Pro Gly Leu Glu His Ala His Ile Trp Phe Ser Ile Pro Ile Cys
             20                  25                  30 ctc atg tac ctg ctt gcc atc atg ggc aac tgc acc att ctc ttt att   144
Leu Met Tyr Leu Leu Ala Ile Met Gly Asn Cys Thr Ile Leu Phe Ile
             35                  40                  45
```

| | | | | | | | | | | | | | | | | |
|---|---|---|---|---|---|---|---|---|---|---|---|---|---|---|---|---|
| ata | aag | aca | gag | ccc | tcg | ctt | cat | gag | ccc | atg | tat | tat | ttc | ctt | gcc | 192 |
| Ile | Lys | Thr | Glu | Pro | Ser | Leu | His | Glu | Pro | Met | Tyr | Tyr | Phe | Leu | Ala | |
| | 50 | | | | 55 | | | | 60 | | | | | | | |
| atg | ttg | gct | gtc | tct | gac | atg | ggc | ctg | tcc | ctc | tcc | tcc | ctt | cct | acc | 240 |
| Met | Leu | Ala | Val | Ser | Asp | Met | Gly | Leu | Ser | Leu | Ser | Ser | Leu | Pro | Thr | |
| 65 | | | | | 70 | | | | | 75 | | | | | 80 | |
| atg | ttg | agg | gtc | ttc | ttg | ttc | aat | gcc | atg | gga | att | tca | cct | aat | gcc | 288 |
| Met | Leu | Arg | Val | Phe | Leu | Phe | Asn | Ala | Met | Gly | Ile | Ser | Pro | Asn | Ala | |
| | | | | 85 | | | | | 90 | | | | | 95 | | |
| tgc | ttt | gct | caa | gaa | ttc | ttc | att | cat | gga | ttc | act | gtc | atg | gaa | tcc | 336 |
| Cys | Phe | Ala | Gln | Glu | Phe | Phe | Ile | His | Gly | Phe | Thr | Val | Met | Glu | Ser | |
| | | | 100 | | | | | 105 | | | | | 110 | | | |
| tca | gta | ctt | cta | att | atg | tct | ttg | gac | cgc | ttt | ctt | gcc | att | cac | aat | 384 |
| Ser | Val | Leu | Leu | Ile | Met | Ser | Leu | Asp | Arg | Phe | Leu | Ala | Ile | His | Asn | |
| | | 115 | | | | | 120 | | | | | 125 | | | | |
| ccc | tta | aga | tac | agt | tct | atc | ctc | act | agc | aac | agg | gtt | gct | aaa | atg | 432 |
| Pro | Leu | Arg | Tyr | Ser | Ser | Ile | Leu | Thr | Ser | Asn | Arg | Val | Ala | Lys | Met | |
| | 130 | | | | | 135 | | | | | 140 | | | | | |
| gga | ctt | att | tta | gcc | att | agg | agc | att | ctc | tta | gtg | att | cca | ttt | ccc | 480 |
| Gly | Leu | Ile | Leu | Ala | Ile | Arg | Ser | Ile | Leu | Leu | Val | Ile | Pro | Phe | Pro | |
| 145 | | | | | 150 | | | | | 155 | | | | | 160 | |
| ttc | acc | tta | agg | aga | tta | aaa | tat | tgt | caa | aag | aat | ctt | ctt | tct | cac | 528 |
| Phe | Thr | Leu | Arg | Arg | Leu | Lys | Tyr | Cys | Gln | Lys | Asn | Leu | Leu | Ser | His | |
| | | | | 165 | | | | | 170 | | | | | 175 | | |
| tca | tac | tgt | ctt | cat | cag | gat | acc | atg | aag | ctg | gcc | tgc | tct | gac | aac | 576 |
| Ser | Tyr | Cys | Leu | His | Gln | Asp | Thr | Met | Lys | Leu | Ala | Cys | Ser | Asp | Asn | |
| | | | | 180 | | | | | 185 | | | | | 190 | | |
| aag | acc | aat | gtc | atc | tat | ggc | ttc | ttc | att | gct | ctc | tgt | act | atg | ctg | 624 |
| Lys | Thr | Asn | Val | Ile | Tyr | Gly | Phe | Phe | Ile | Ala | Leu | Cys | Thr | Met | Leu | |
| | | | 195 | | | | | 200 | | | | | 205 | | | |
| gac | ttg | gca | ctg | att | gtt | ttg | tct | tat | gtg | ctg | atc | ttg | aag | act | ata | 672 |
| Asp | Leu | Ala | Leu | Ile | Val | Leu | Ser | Tyr | Val | Leu | Ile | Leu | Lys | Thr | Ile | |
| | | 210 | | | | | 215 | | | | | 220 | | | | |
| ctc | agc | att | gca | tct | ttg | gca | gag | agg | ctt | aag | gcc | cta | aat | acc | tgt | 720 |
| Leu | Ser | Ile | Ala | Ser | Leu | Ala | Glu | Arg | Leu | Lys | Ala | Leu | Asn | Thr | Cys | |
| 225 | | | | | 230 | | | | | 235 | | | | | 240 | |
| gtc | tcc | cac | atc | tgt | gct | gtg | ctc | acc | ttc | tat | gtg | ccc | atc | atc | acc | 768 |
| Val | Ser | His | Ile | Cys | Ala | Val | Leu | Thr | Phe | Tyr | Val | Pro | Ile | Ile | Thr | |
| | | | | 245 | | | | | 250 | | | | | 255 | | |
| ctg | gct | gcc | atg | cat | cac | ttt | gcc | aag | cac | aaa | agc | cct | ctt | gtt | gtg | 816 |
| Leu | Ala | Ala | Met | His | His | Phe | Ala | Lys | His | Lys | Ser | Pro | Leu | Val | Val | |
| | | | | 260 | | | | | 265 | | | | | 270 | | |
| atc | ctt | att | gca | gat | atg | ttc | ttg | ttg | gtg | ccg | ccc | ctt | atg | aac | ccc | 864 |
| Ile | Leu | Ile | Ala | Asp | Met | Phe | Leu | Leu | Val | Pro | Pro | Leu | Met | Asn | Pro | |
| | | | | 275 | | | | | 280 | | | | | 285 | | |
| att | gtg | tac | tgt | gta | aag | act | cga | caa | atc | tgg | gag | aag | atc | ttg | ggg | 912 |
| Ile | Val | Tyr | Cys | Val | Lys | Thr | Arg | Gln | Ile | Trp | Glu | Lys | Ile | Leu | Gly | |
| | | | | 290 | | | | | 295 | | | | | 300 | | |
| aag | ttg | ctt | aat | gta | tgt | ggg | aga | taa | | | | | | | | 939 |
| Lys | Leu | Leu | Asn | Val | Cys | Gly | Arg | | | | | | | | | |
| 305 | | | | 310 | | | | | | | | | | | | |

<210> SEQ ID NO 20
<211> LENGTH: 312
<212> TYPE: PRT
<213> ORGANISM: Homo sapiens

<400> SEQUENCE: 20

Met Ser Val Leu Asn Asn Ser Glu Val Lys Leu Phe Leu Leu Ile Gly
1               5                   10                  15

```
Ile Pro Gly Leu Glu His Ala His Ile Trp Phe Ser Ile Pro Ile Cys
         20                  25                  30

Leu Met Tyr Leu Leu Ala Ile Met Gly Asn Cys Thr Ile Leu Phe Ile
         35                  40                  45

Ile Lys Thr Glu Pro Ser Leu His Glu Pro Met Tyr Tyr Phe Leu Ala
 50                  55                  60

Met Leu Ala Val Ser Asp Met Gly Leu Ser Leu Ser Ser Leu Pro Thr
 65                  70                  75                  80

Met Leu Arg Val Phe Leu Phe Asn Ala Met Gly Ile Ser Pro Asn Ala
                 85                  90                  95

Cys Phe Ala Gln Glu Phe Phe Ile His Gly Phe Thr Val Met Glu Ser
            100                 105                 110

Ser Val Leu Leu Ile Met Ser Leu Asp Arg Phe Leu Ala Ile His Asn
        115                 120                 125

Pro Leu Arg Tyr Ser Ser Ile Leu Thr Ser Asn Arg Val Ala Lys Met
    130                 135                 140

Gly Leu Ile Leu Ala Ile Arg Ser Ile Leu Leu Val Ile Pro Phe Pro
145                 150                 155                 160

Phe Thr Leu Arg Arg Leu Lys Tyr Cys Gln Lys Asn Leu Leu Ser His
                165                 170                 175

Ser Tyr Cys Leu His Gln Asp Thr Met Lys Leu Ala Cys Ser Asp Asn
            180                 185                 190

Lys Thr Asn Val Ile Tyr Gly Phe Phe Ile Ala Leu Cys Thr Met Leu
        195                 200                 205

Asp Leu Ala Leu Ile Val Leu Ser Tyr Val Leu Ile Leu Lys Thr Ile
    210                 215                 220

Leu Ser Ile Ala Ser Leu Ala Glu Arg Leu Lys Ala Leu Asn Thr Cys
225                 230                 235                 240

Val Ser His Ile Cys Ala Val Leu Thr Phe Tyr Val Pro Ile Ile Thr
                245                 250                 255

Leu Ala Ala Met His His Phe Ala Lys His Lys Ser Pro Leu Val Val
            260                 265                 270

Ile Leu Ile Ala Asp Met Phe Leu Leu Val Pro Pro Leu Met Asn Pro
        275                 280                 285

Ile Val Tyr Cys Val Lys Thr Arg Gln Ile Trp Glu Lys Ile Leu Gly
    290                 295                 300

Lys Leu Leu Asn Val Cys Gly Arg
305                 310

<210> SEQ ID NO 21
<211> LENGTH: 2445
<212> TYPE: DNA
<213> ORGANISM: Bos taurus
<220> FEATURE:
<221> NAME/KEY: CDS
<222> LOCATION: (1)..(1047)

<400> SEQUENCE: 21 atg aac ggg acc gag ggc cca aac ttc tac gtg cct ttc tcc aac aag      48
Met Asn Gly Thr Glu Gly Pro Asn Phe Tyr Val Pro Phe Ser Asn Lys
1               5                   10                  15 acg ggc gtg gtg cgc agc ccc ttc gag gcc ccg cag tac tac ctg gcg      96
Thr Gly Val Val Arg Ser Pro Phe Glu Ala Pro Gln Tyr Tyr Leu Ala
            20                  25                  30 gag cca tgg cag ttc tcc atg ctg gcc gcc tac atg ttc ctg ctg atc     144
Glu Pro Trp Gln Phe Ser Met Leu Ala Ala Tyr Met Phe Leu Leu Ile
        35                  40                  45
```

-continued

```
atg ctt ggc ttc ccc atc aac ttc ctc acg ctg tac gtc aca gtc cag        192
Met Leu Gly Phe Pro Ile Asn Phe Leu Thr Leu Tyr Val Thr Val Gln
     50                  55                  60 cac aag aag ctg cgc aca ccc ctc aac tac atc ctg ctc aac ctg gcc        240
His Lys Lys Leu Arg Thr Pro Leu Asn Tyr Ile Leu Leu Asn Leu Ala
 65                  70                  75                  80 gtg gcc gac ctc ttc atg gtc ttc ggg ggc ttc acc acc acc ctc tac        288
Val Ala Asp Leu Phe Met Val Phe Gly Gly Phe Thr Thr Thr Leu Tyr
                     85                  90                  95 acc tct ctg cac gga tac ttc gtc ttt ggg ccc acg ggc tgc aac ctg        336
Thr Ser Leu His Gly Tyr Phe Val Phe Gly Pro Thr Gly Cys Asn Leu
                100                 105                 110 gag ggc ttc ttt gcc acc ctg ggc ggt gaa att gca ctg tgg tcc ttg        384
Glu Gly Phe Phe Ala Thr Leu Gly Gly Glu Ile Ala Leu Trp Ser Leu
            115                 120                 125 gtg gtc ctg gcc atc gag cgg tac gtg gtg gtg tgc aag ccc atg agc        432
Val Val Leu Ala Ile Glu Arg Tyr Val Val Val Cys Lys Pro Met Ser
    130                 135                 140 aac ttc cgc ttc ggg gag aac cac gcc atc atg ggc gtc gcc ttc acc        480
Asn Phe Arg Phe Gly Glu Asn His Ala Ile Met Gly Val Ala Phe Thr
145                 150                 155                 160 tgg gtc atg gct ctg gcc tgt gcc gcg ccc ccc ctc gtc ggc tgg tcc        528
Trp Val Met Ala Leu Ala Cys Ala Ala Pro Pro Leu Val Gly Trp Ser
                165                 170                 175 agg tac atc ccg gag ggc atg cag tgc tcg tgc ggg att gac tac tac        576
Arg Tyr Ile Pro Glu Gly Met Gln Cys Ser Cys Gly Ile Asp Tyr Tyr
                180                 185                 190 acg ccc cac gag gag acc aac aat gag tcg ttc gtc atc tac atg ttc        624
Thr Pro His Glu Glu Thr Asn Asn Glu Ser Phe Val Ile Tyr Met Phe
            195                 200                 205 gtg gtc cac ttc atc atc ccc ctg att gtc ata ttc ttc tgc tac ggg        672
Val Val His Phe Ile Ile Pro Leu Ile Val Ile Phe Phe Cys Tyr Gly
    210                 215                 220 cag ctg gtg ttc acc gtc aag gag gcg gct gcc cag cag cag gag tcg        720
Gln Leu Val Phe Thr Val Lys Glu Ala Ala Ala Gln Gln Gln Glu Ser
225                 230                 235                 240 gcc acc act cag aag gcc gag aag gag gtc acc cgc atg gtg atc atc        768
Ala Thr Thr Gln Lys Ala Glu Lys Glu Val Thr Arg Met Val Ile Ile
                245                 250                 255 atg gtc atc gct ttc cta atc tgc tgg ctg ccc tac gct ggg gtg gcg        816
Met Val Ile Ala Phe Leu Ile Cys Trp Leu Pro Tyr Ala Gly Val Ala
                260                 265                 270 ttc tac atc ttc acc cat cag ggc tct gac ttt ggc ccc atc ttc atg        864
Phe Tyr Ile Phe Thr His Gln Gly Ser Asp Phe Gly Pro Ile Phe Met
            275                 280                 285 acc atc ccg gct ttc ttt gcc aag act tct gcc gtc tac aac ccc gtc        912
Thr Ile Pro Ala Phe Phe Ala Lys Thr Ser Ala Val Tyr Asn Pro Val
    290                 295                 300 atc tac atc atg atg aac aag cag ttc cgg aac tgc atg gtc acc act        960
Ile Tyr Ile Met Met Asn Lys Gln Phe Arg Asn Cys Met Val Thr Thr
305                 310                 315                 320 ctc tgc tgt ggc aag aac ccg ctg ggt gac gac gag gcc tcc acc acc       1008
Leu Cys Cys Gly Lys Asn Pro Leu Gly Asp Asp Glu Ala Ser Thr Thr
                325                 330                 335 gtc tcc aag aca gag acc agc cag gtg gcg cct gcc taa gcccctccag       1057
Val Ser Lys Thr Glu Thr Ser Gln Val Ala Pro Ala
                340                 345 ggactccgtg gccagctgca ggagtccctc agcccccacc ccaccccagc ctcagcagct    1117
```

```
ccatcaggag ccgcgcctgt cggaaccagc tctcacaggc tccctgagtg taaacacaaa    1177
gaccaaccaa ccaaatgcaa aagaatcaac gagagaaaca ggaggcgcct cacgtggcag    1237
gggcggcccg atctggagtc ctgatttccc gggggcccgc tgtagatcca ctcccccag    1297 ctcatctctc agctacacaa gagctcttgc tctggaaaag tgtcccagct tagggataag    1357
tgagtagcac atgacggggc atgccgtagg tgcttattaa taaatgctag gtggaggaaa    1417
gaaggaatga atggagagat gaacgggtcg ggagggcata ggcatcctct tacaacatgt    1477
tagcagcagc agcagcagct cgcccttggc tcatgacctt gagcagctgt tttgtccttg    1537
ggcctcactt tcttccccca tacaatggga attccaaatc tctcctcaca cgggctgctg    1597
ggaagatcaa atgagattgt gtgtgtgtgc gtgcgtgcgt gctcgcttgt gtgagctctt    1657
tgtaaatagt aaggagctgg acagactgta gttaacatta tgaataatat caagtaatat    1717
aagtaattca tctcctatga tcatctcctc ttgatagcga ccactttgag actgggcaag    1777
gctctaagca tccagcctcg tcaggcttat aaacattaga cagatggcaa ggtcagacca    1837
gcgccgggtg gtgggccaca gggaaggacg gtcaaggaaa tgcagagtgc aggcatcagg    1897
cctgagaaga aaacaaaaac caaaaaaaca acatcagagg accagagtct ggggccagtg    1957
cagagccccc atgacgcggg ccactccctc ccagtgcaac cccagagag acaggtcttg     2017 ctctcggcat ctgaaaaacc actagctctc ctgcccagca cccaggctgc agtatctctg    2077
ggcccgtatg gagcttctag aagttatgtt tacctgccca catttaacga agagctgggt    2137
ccccaacatc acctttgtct caaaagagc ttaaaaaaca aaagcgtggg aaatccggct     2197
ggacccacct tccccctggg aagttcacag atcacagatt ttagctccct tgctgggcaa    2257
gccttcagcg gctccagtcc attctccact ccggagagtc cttgctgctg agaggctggc    2317
tgggactcta ggacatcaga atcgagccgc ctcataactg cccctcctcc actacataac    2377
caaagcggga agctctacct ctccccagct ctgcctggag acgaaggcaa attggggtat    2437
taaaagct                                                             2445
```

<210> SEQ ID NO 22
<211> LENGTH: 348
<212> TYPE: PRT
<213> ORGANISM: Bos taurus

<400> SEQUENCE: 22

```
Met Asn Gly Thr Glu Gly Pro Asn Phe Tyr Val Pro Phe Ser Asn Lys
1               5                   10                  15

Thr Gly Val Val Arg Ser Pro Phe Glu Ala Pro Gln Tyr Tyr Leu Ala
            20                  25                  30

Glu Pro Trp Gln Phe Ser Met Leu Ala Ala Tyr Met Phe Leu Leu Ile
        35                  40                  45

Met Leu Gly Phe Pro Ile Asn Phe Leu Thr Leu Tyr Val Thr Val Gln
    50                  55                  60

His Lys Lys Leu Arg Thr Pro Leu Asn Tyr Ile Leu Leu Asn Leu Ala
65                  70                  75                  80

Val Ala Asp Leu Phe Met Val Phe Gly Gly Phe Thr Thr Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Val Cys Lys Pro Met Ser
```

```
                130             135                 140
Asn Phe Arg Phe Gly Glu Asn His Ala Ile Met Gly Val Ala Phe Thr
145                     150                 155                 160

Trp Val Met Ala Leu Ala Cys Ala Ala Pro Pro Leu Val Gly Trp Ser
                165                 170                 175

Arg Tyr Ile Pro Glu Gly Met Gln Cys Ser Cys Gly Ile Asp Tyr Tyr
                180                 185                 190

Thr Pro His Glu Glu Thr Asn Asn Glu Ser Phe Val Ile Tyr Met Phe
            195                 200                 205

Val Val His Phe Ile Ile Pro Leu Ile Val Ile Phe Phe Cys Tyr Gly
            210                 215                 220

Gln Leu Val Phe Thr Val Lys Glu Ala Ala Ala Gln Gln Gln Glu Ser
225                 230                 235                 240

Ala Thr Thr Gln Lys Ala Glu Lys Glu Val Thr Arg Met Val Ile Ile
                245                 250                 255

Met Val Ile Ala Phe Leu Ile Cys Trp Leu Pro Tyr Ala Gly Val Ala
                260                 265                 270

Phe Tyr Ile Phe Thr His Gln Gly Ser Asp Phe Gly Pro Ile Phe Met
            275                 280                 285

Thr Ile Pro Ala Phe Phe Ala Lys Thr Ser Ala Val Tyr Asn Pro Val
    290                 295                 300

Ile Tyr Ile Met Met Asn Lys Gln Phe Arg Asn Cys Met Val Thr Thr
305                 310                 315                 320

Leu Cys Cys Gly Lys Asn Pro Leu Gly Asp Asp Glu Ala Ser Thr Thr
                325                 330                 335

Val Ser Lys Thr Glu Thr Ser Gln Val Ala Pro Ala
                340                 345
```

SCREENING METHOD FOR MATERIALS THAT SUPPRESS CHARACTERISTIC BODY ODOR OF ELDERLY PEOPLE

CROSS-REFERENCE TO RELATED APPLICATIONS

This application is the U.S. National Stage of PCT/JP2018/047918, filed Dec. 26, 2018, which claims priority to JP 2017-252587, filed Dec. 27, 2017.

The instant application contains a Sequence Listing which has been submitted in ASCII format via EFS-WEB and is hereby incorporated by reference in its entirety. Said ASCII copy, created on Jun. 18, 2020, is named sequence.txt and is 85,275 bytes.

TECHNICAL FIELD

The present invention relates to a screening method for materials that suppress the characteristic body odor of elderly people. The present invention also relates to a screening method for trans-2-nonenal odor suppressors and further relates to a screening method for trans-2-octenal odor suppressors.

BACKGROUND ART

Ambient odors and malodors perceived as unpleasant in daily life are strongly desired to be eliminated more effectively for improved living environments. In recent years, there has been growing awareness of body odors, among others.

Body odors are broadly divided into two categories, i.e., the "smell of each body part" (e.g., mouth odor, foot odor, armpit odor, scalp odor) and the "combined smell arising from the body trunk." The "combined smell arising from the body trunk" is known to change with age, and the characteristic body odor of elderly people, which is observed at middle age or later, very strongly tends to be disfavored. As to substances responsible for this characteristic body odor of elderly people, unsaturated aldehydes such as nonenal and octenal have been reported to cause this odor (Patent Literature 1). Unsaturated aldehydes such as nonenal and octenal have also been known as off-flavors in beverages (e.g., Non-patent Literature 1).

CITATION LIST

Patent Literature

Patent Literature 1: JP H11-286423 A

Non Patent Literature

Non-patent Literature 1: "The recent findings in the off-flavors of beer" Toru Kishimoto, Journal of Japan Association on Odor Environment, Volume 44, Issue 1 (2013)

SUMMARY OF INVENTION

Technical Problem

Screening may be possible for candidate substances for materials that suppress the characteristic body odor of elderly people when olfactory receptors responding to known substances responsible for the characteristic body odor of elderly people are searched and used for this purpose. However, such olfactory receptors responding to substances responsible for the characteristic body odor of elderly people have not been known so far.

Under these circumstances, there has been a desire to search for olfactory receptors responding to substances responsible for the characteristic body odor of elderly people and thereby provide a screening method for candidate substances for materials that suppress the characteristic body odor of elderly people. Moreover, there has also been a desire to search for olfactory receptors responding to unsaturated aldehydes, which are substances responsible not only for the characteristic body odor of elderly people but also for off-flavors in beverages, and thereby provide a screening method for candidate substances for unsaturated aldehyde odor suppressors.

Solution to Problem

As a result of extensive and intensive efforts made to solve the problems stated above, the inventors of the present invention have succeeded in newly identifying respective olfactory receptors responding to trans-2-nonenal and trans-2-octenal, which are substances responsible for the characteristic body odor of elderly people and are members of unsaturated aldehydes. The inventors of the present invention have made further studies and have found that the use of these olfactory receptors enables the evaluation and selection of materials that suppress the characteristic body odor of elderly people and further trans-2-nonenal odor suppressors and trans-2-octenal odor suppressors by means of the masking effect of olfactory receptor antagonists.

Namely, the present invention provides a screening method for candidate substances for materials that suppress the characteristic body odor of elderly people, as shown below. Moreover, the present invention also provides a screening method for trans-2-nonenal odor suppressors and further provides a screening method for trans-2-octenal odor suppressors, as shown below.

[1] A screening method for materials that suppress the characteristic body odor of elderly people, which comprises the following steps:

adding a test substance and a substance responsible for the characteristic body odor of elderly people to at least one olfactory receptor polypeptide selected from the group consisting of (a) OR2C1, OR2J2, OR4E2 and OR5P3, and (b) polypeptides which comprise an amino acid sequence sharing an identity of at least 80% with the amino acid sequence of any of the polypeptides in (a) and which are responsive to the substance responsible for the characteristic body odor of elderly people;

measuring the response of the olfactory receptor polypeptide to the substance responsible for the characteristic body odor of elderly people; and identifying a test substance that suppresses the response of the olfactory receptor polypeptide on the basis of the measured response.

[2] The method according to [1] above, wherein the substance responsible for the characteristic body odor of elderly people is at least one selected from the group consisting of trans-2-nonenal and trans-2-octenal.

[3] The method according to any of [1] or [2] above, wherein the response of the olfactory receptor polypeptide is measured on cells isolated from a living body expressing the olfactory receptor polypeptide or on cells genetically engineered to artificially express the olfactory receptor polypeptide.

[4] The method according to any of [1] to [3] above, wherein the response of the olfactory receptor polypeptide is measured by a reporter assay.

[5] A screening method for trans-2-nonenal odor suppressors, which comprises the following steps:

adding a test substance and trans-2-nonenal to at least one olfactory receptor polypeptide selected from the group consisting of (a) OR1D2, OR2C1, OR2J2, OR4E2, OR5P3 and OR52N2, and (b) polypeptides which comprise an amino acid sequence sharing an identity of at least 80% with the amino acid sequence of any of the polypeptides in (a) and which are responsive to trans-2-nonenal;

measuring the response of the olfactory receptor polypeptide to trans-2-nonenal; and identifying a test substance that suppresses the response of the olfactory receptor polypeptide on the basis of the measured response.

[6] The method according to [5] above, wherein the response of the olfactory receptor polypeptide is measured on cells isolated from a living body expressing the olfactory receptor polypeptide or on cells genetically engineered to artificially express the olfactory receptor polypeptide.

[7] The method according to any of [5] or [6] above, wherein the response of the olfactory receptor polypeptide is measured by a reporter assay.

[8] A screening method for trans-2-octenal odor suppressors, which comprises the following steps:

adding a test substance and trans-2-octenal to at least one olfactory receptor polypeptide selected from the group consisting of (a) OR2C1, OR2J2, OR2J3, OR4E2, OR5P3, OR7G1, OR9I1 and OR51A7, and (b) polypeptides which comprise an amino acid sequence sharing an identity of at least 80% with the amino acid sequence of any of the polypeptides in (a) and which are responsive to trans-2-octenal;

measuring the response of the olfactory receptor polypeptide to trans-2-octenal; and identifying a test substance that suppresses the response of the olfactory receptor polypeptide on the basis of the measured response.

[9] The method according to [8] above, wherein the response of the olfactory receptor polypeptide is measured on cells isolated from a living body expressing the olfactory receptor polypeptide or on cells genetically engineered to artificially express the olfactory receptor polypeptide.

[10] The method according to any of [8] or [9] above, wherein the response of the olfactory receptor polypeptide is measured by a reporter assay.

Advantageous Effects of Invention

The method of the present invention allows screening of test substances to select candidate substances for materials that suppress the characteristic body odor of elderly people, which are capable of inhibiting the binding between substances responsible for the characteristic body odor of elderly people and olfactory receptor polypeptides. Moreover, the method of the present invention allows screening for candidate substances for trans-2-nonenal odor suppressors and trans-2-octenal odor suppressors. The screening method of the present invention can be expected to contribute to the development of materials that suppress the characteristic body odor of elderly people, trans-2-nonenal odor suppressors and trans-2-octenal odor suppressors. Moreover, when attempting to develop new aroma ingredients, there are problems of olfactory fatigue and variations among individuals if many candidate substances are evaluated for their odor by the human olfactory sense alone; and hence the proper selection of candidate substances may involve difficulties. According to the method of the present invention, such problems can be overcome or reduced.

DESCRIPTION OF EMBODIMENTS

Figure 1:
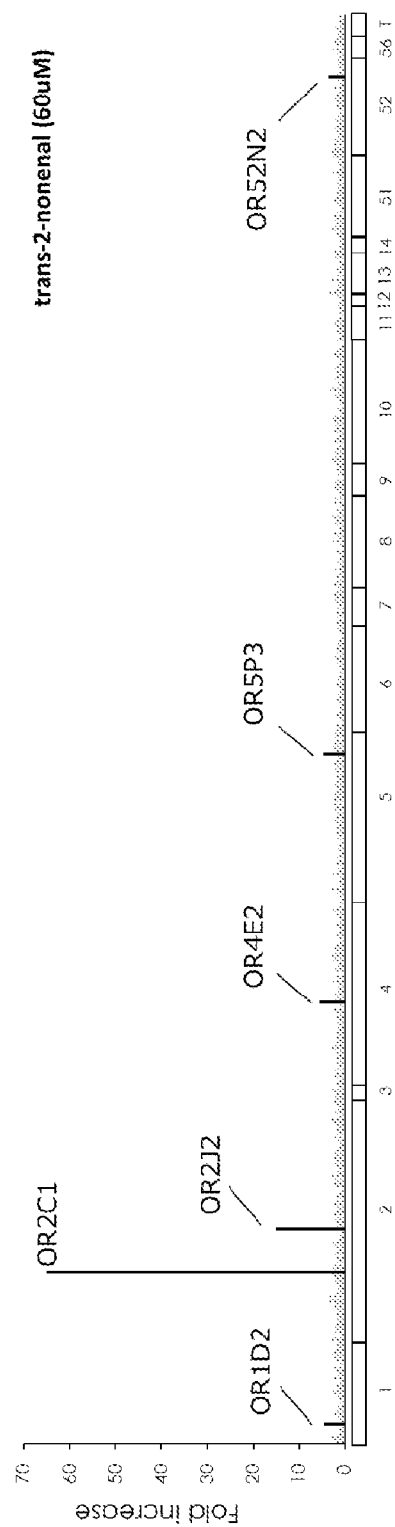
FIG. 1 shows the results measured for the responses of various olfactory receptor polypeptides to trans-2-nonenal.
Figure 2:
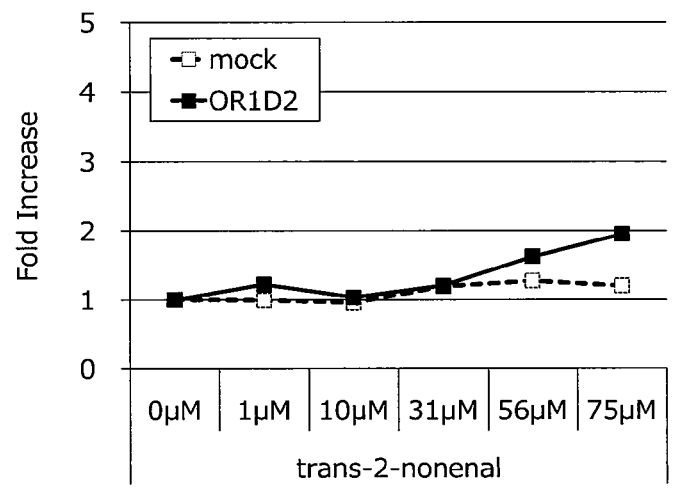
FIG. 2 shows the results measured for the response of olfactory receptor OR1D2 to trans-2-nonenal.
Figure 3:
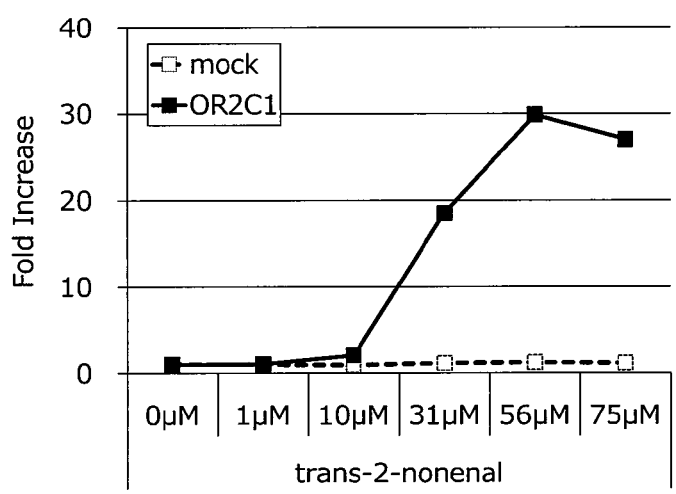
FIG. 3 shows the results measured for the response of olfactory receptor OR2C1 to trans-2-nonenal.
Figure 4:
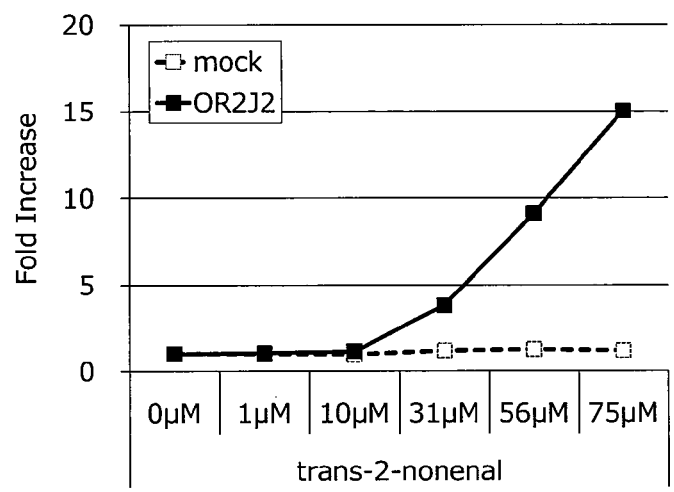
FIG. 4 shows the results measured for the response of olfactory receptor OR2J2 to trans-2-nonenal.
Figure 5:
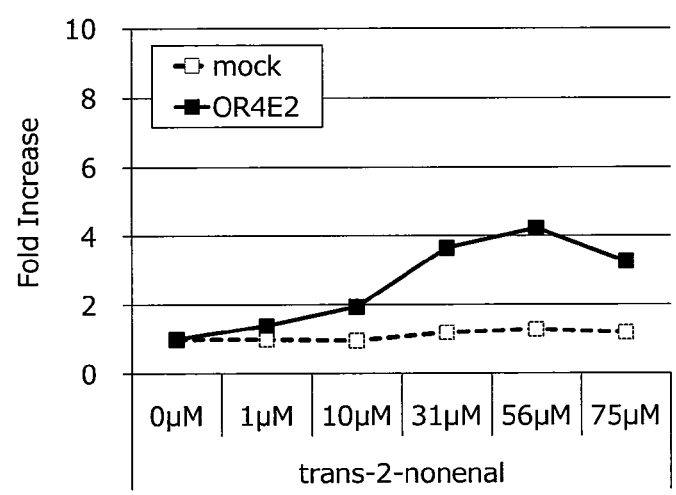
FIG. 5 shows the results measured for the response of olfactory receptor OR4E2 to trans-2-nonenal.
Figure 6:
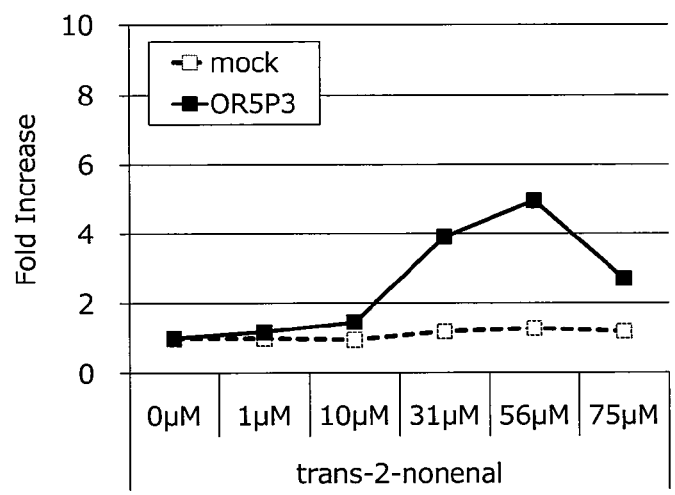
FIG. 6 shows the results measured for the response of olfactory receptor OR5P3 to trans-2-nonenal.
Figure 7:
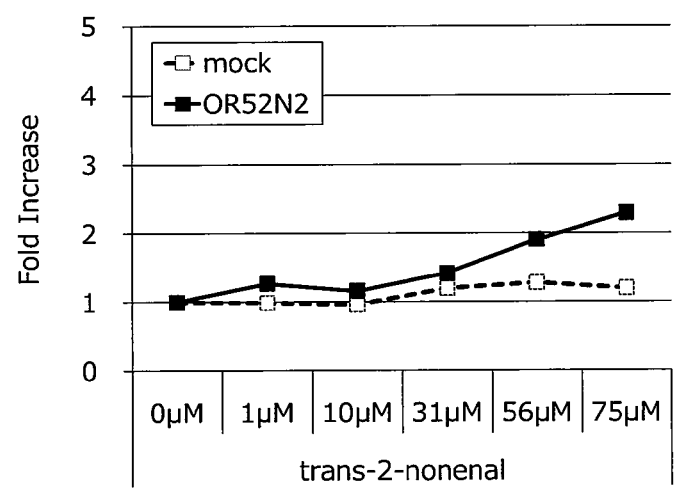
FIG. 7 shows the results measured for the response of olfactory receptor OR52N2 to trans-2-nonenal.

The screening method of the present invention will be described in more detail below.

1. Screening Method for Materials that Suppress the Characteristic Body Odor of Elderly People The screening method for materials that suppress the characteristic body odor of elderly people according to the present invention is designed such that test substances are screened with olfactory receptor polypeptides responsive to substances responsible for the characteristic body odor of elderly people to select candidate substances for materials that suppress the characteristic body odor of elderly people. This method is characterized by comprising the following steps:

adding a test substance and a substance responsible for the characteristic body odor of elderly people to at least one olfactory receptor polypeptide selected from the group consisting of (a) OR2C1, OR2J2, OR4E2 and OR5P3, and (b) polypeptides which comprise an amino acid sequence sharing an identity of at least 80% with the amino acid sequence of any of the polypeptides in (a) and which are responsive to the substance responsible for the characteristic body odor of elderly people;

measuring the response of the olfactory receptor polypeptide to the substance responsible for the characteristic body odor of elderly people; and identifying a test substance that suppresses the response of the olfactory receptor polypeptide on the basis of the measured response.

According to a preferred embodiment of the present invention, the screening method for materials that suppress the characteristic body odor of elderly people comprises the following steps:

(i) bringing an olfactory receptor polypeptide selected from the group consisting of (a) OR2C1, OR2J2, OR4E2 and OR5P3, and (b) polypeptides which comprise an amino acid sequence sharing an identity of 80% or more with the amino acid sequence of any of the polypeptides in (a) and which are responsive to a substance responsible for the characteristic body odor of elderly people into contact with the substance responsible for the characteristic body odor of elderly people to measure the response of the olfactory receptor polypeptide to the substance responsible for the characteristic body odor of elderly people;
(ii) mixing a test substance with the substance responsible for the characteristic body odor of elderly people to measure the response of the olfactory receptor polypeptide used in step (i); and
(iii) comparing the results measured in steps (i) and (ii) to select a test substance causing a reduction in the response as a candidate substance for materials that suppress the characteristic body odor of elderly people.

The screening method for materials that suppress the characteristic body odor of elderly people according to the present invention is configured such that candidate substances for materials that suppress the characteristic body odor of elderly people are selected from among test substances on the basis of the responsiveness of each test substance to an olfactory receptor polypeptide selected from the group consisting of OR2C1, OR2J2, OR4E2, OR5P3, and polypeptides which comprise amino acid sequences sharing an identity of 80% or more with the amino acid sequences of these polypeptides and which are responsive to substances responsible for the characteristic body odor of elderly people.

A single olfactory receptor is known to respond to several types of structurally similar odorous compounds. Thus, when olfactory receptor polypeptides responsive to known substances responsible for the characteristic body odor of elderly people are identified and test substances are evaluated for their responsiveness to these olfactory receptor polypeptides, candidate substances capable of preventing known substances responsible for the characteristic body odor of elderly people from binding to the olfactory receptor polypeptides can be selected from among the test substances. As used herein, the term "test substance" is not limited in any way, but it refers to a subject to be tested for its suppressive effect on the characteristic body odor of elderly people and is intended to mean a compound, a composition or a mixture. Likewise, as used herein, the expression "material that suppresses the characteristic body odor of elderly people" is not limited in any way, but it is intended to mean a compound, a composition or a mixture, which is capable of suppressing the characteristic body odor of elderly people. An explanation will be given below of each step in the screening method of the present invention.
<Step (i)>
In step (i), an olfactory receptor polypeptide selected from the group consisting of OR2C1, OR2J2, OR4E2, OR5P3, and polypeptides which comprise an amino acid sequence sharing an identity of 80% or more with the amino acid sequence of any of these polypeptides and which are responsive to a substance responsible for the characteristic body odor of elderly people is brought into contact with the substance responsible for the characteristic body odor of elderly people to measure the response of the olfactory receptor polypeptide to the substance responsible for the characteristic body odor of elderly people.

The olfactory receptor polypeptide to be used for this purpose is an olfactory receptor polypeptide selected from the group consisting of OR2C1, OR2J2, OR4E2, OR5P3, and polypeptides which comprise an amino acid sequence sharing an identity of 80% or more with the amino acid sequence of any of these polypeptides and which are responsive to a substance responsible for the characteristic body odor of elderly people.

OR2C1 has been registered in GenBank under NM_012368 and is a polypeptide consisting of an amino acid sequence (SEQ ID NO: 2) encoded by DNA having the nucleotide sequence shown in SEQ ID NO: 1.

OR2J2 has been registered in GenBank under NM_030905 and is a polypeptide consisting of an amino acid sequence (SEQ ID NO: 4) encoded by DNA having the nucleotide sequence shown in SEQ ID NO: 3.

OR4E2 has been registered in GenBank under NM_001001912 and is a polypeptide consisting of an amino acid sequence (SEQ ID NO: 6) encoded by DNA having the nucleotide sequence shown in SEQ ID NO: 5.

OR5P3 has been registered in GenBank under NM_153445 and is a polypeptide consisting of an amino acid sequence (SEQ ID NO: 8) encoded by DNA having the nucleotide sequence shown in SEQ ID NO: 7.

Since these polypeptides strongly respond selectively to trans-2-nonenal and trans-2-octenal, the screening method using OR2C1, OR2J2, OR4E2 and/or OR5P3 can be expected to contribute to the development of materials that suppress the characteristic body odor of elderly people.

As an olfactory receptor, it is also possible to use an olfactory receptor polypeptide selected from the group consisting of polypeptides which comprise an amino acid sequence sharing an identity of 80% or more, preferably 85% or more, more preferably 90% or more, even more preferably 95% or more, and particularly preferably 98% or more with the amino acid sequence possessed by any of these polypeptides (i.e., SEQ ID NO: 2, 4, 6 or 8) and which are responsive to a substance responsible for the characteristic body odor of elderly people. It should be noted that the sequence identity of amino acid sequences is calculated herein by the BLAST search algorithm (publicly available from NCBI).

Such olfactory receptor polypeptides may be used alone, or two or more of them may be used in combination.

In the present invention, as a substance responsible for the characteristic body odor of elderly people, at least one selected from the group consisting of trans-2-nonenal and trans-2-octenal may be preferred for use.

In the present invention, there is no particular limitation on how to contact an olfactory receptor polypeptide with a substance responsible for the characteristic body odor of elderly people to measure the response of the olfactory receptor polypeptide to the substance responsible for the characteristic body odor of elderly people. For example, the response of the olfactory receptor polypeptide may be measured by being contacted with the substance responsible for the characteristic body odor of elderly people on cells isolated from a living body expressing the olfactory receptor polypeptide, or alternatively, the response of the olfactory receptor polypeptide may be measured by being contacted with the substance responsible for the characteristic body odor of elderly people on cells genetically engineered to artificially express the olfactory receptor polypeptide. The time required to contact the olfactory receptor polypeptide with the substance responsible for the characteristic body odor of elderly people is not determined exactly because of also depending on the concentration of the substance responsible for the characteristic body odor of elderly people, but it is usually 2 to 4 hours. The same goes for when the olfactory receptor polypeptide is contacted with the substance responsible for the characteristic body odor of elderly people in admixture with a test substance.

Cells genetically engineered to artificially express the olfactory receptor polypeptide may be prepared when cells are transformed with a vector carrying a gene encoding the olfactory receptor polypeptide.

In a preferred embodiment of the present invention, the N-terminal 20 amino acid residues of bovine rhodopsin may be integrated together with the olfactory receptor polypeptide. Upon integration of the N-terminal 20 amino acid residues of bovine rhodopsin, cell membrane expression of the olfactory receptor polypeptide may be facilitated.

Bovine rhodopsin has been registered in GenBank under NM_001014890. Bovine rhodopsin is a polypeptide consisting of an amino acid sequence (SEQ ID NO: 22) encoded by DNA at positions 1 to 1047 of the nucleotide sequence shown in SEQ ID NO: 21.

Moreover, instead of bovine rhodopsin, it is possible to use a polypeptide which comprises an amino acid sequence sharing an identity of 80% or more, preferably 85% or more, more preferably 90% or more, even more preferably 95% or more, and particularly preferably 98% or more with the amino acid sequence shown in SEQ ID NO: 22 and which is capable of facilitating cell membrane expression of the olfactory receptor polypeptide.

It should be noted that amino acid residues of not only bovine rhodopsin but also any other polypeptides may be used as long as they can facilitate cell membrane expression of the olfactory receptor polypeptide.

There is no particular limitation on how to measure the response of the olfactory receptor polypeptide, and any technique used in the art may be used for this purpose. For example, it is known that once an odorous compound has bound to an olfactory receptor polypeptide, G protein in cells will be activated and this G protein will in turn activate adenylate cyclase to convert ATP into cyclic AMP (cAMP), thereby increasing the intracellular level of cAMP. Thus, the response of the olfactory receptor polypeptide can be measured when the level of cAMP is measured. The level of cAMP may be measured using ELISA techniques, reporter gene assay techniques, etc. Above all, it is preferred that the response of the olfactory receptor polypeptide is measured by reporter gene assay techniques using a luminophore (e.g., luciferase).

According to one embodiment of the present invention, the response of the olfactory receptor polypeptide may be evaluated on the basis of the fold increase value determined by dividing the results measured in the presence of a substance responsible for the characteristic body odor of elderly people by the results measured in the absence of the substance responsible for the characteristic body odor of elderly people. For example, when the response of the olfactory receptor polypeptide is measured by reporter gene assay techniques using a luminophore (e.g., luciferase), evaluation can be made using the substance responsible for the characteristic body odor of elderly people at a concentration which gives a fold increase value of preferably 2 or more, more preferably 4 or more, and even more preferably 10 or more.

<Step (ii)>

In step (ii), a test substance is mixed with the substance responsible for the characteristic body odor of elderly people to measure the response of the olfactory receptor used in step (i).

The response of the olfactory receptor polypeptide may be measured in the same manner as shown in step (i), except that the substance responsible for the characteristic body odor of elderly people is mixed with the test substance and contacted with the olfactory receptor polypeptide. For example, the response of the olfactory receptor polypeptide may be measured on cells isolated from a living body expressing the olfactory receptor polypeptide, or alternatively, the response of the olfactory receptor polypeptide may be measured on cells genetically engineered to artificially express the olfactory receptor polypeptide. For proper comparison of the results measured in steps (i) and (ii), the measurement conditions in steps (i) and (ii) are preferably the same, except for the presence or absence of the test substance.

<Step (iii)>

In step (iii), the results measured in steps (i) and (ii) are compared with each other to select a test substance causing a reduction in the response as a candidate substance for materials that suppress the characteristic body odor of elderly people.

In the present invention, when a reduction in the response is observed as a result of comparing the results measured in steps (i) and (ii), the test substance used in step (ii) can be evaluated as a candidate substance for materials that suppress the characteristic body odor of elderly people.

In such a way as described above, test substances can be screened to select candidate substances for materials that suppress the characteristic body odor of elderly people. According to the present invention, it is possible to select candidate substances for materials that suppress the characteristic body odor of elderly people from among many test substances, without causing any problems such as olfactory fatigue and variations among individuals associated with sensory testing by means of the human olfactory sense.

These selected substances can be used as candidate substances for materials that suppress the characteristic body odor of elderly people. If necessary, the selected substances may be subjected to modifications or the like to thereby develop novel compounds having the most suitable odor. Further, the selected substances may be blended with other aroma ingredients to thereby develop aroma ingredients capable of suppressing the characteristic body odor of elderly people and also having the most suitable odor. The screening method of the present invention can be used to contribute to the development of new aroma ingredients serving as materials that suppress the characteristic body odor of elderly people.

2. Screening Method for Trans-2-Nonenal Odor Suppressors

The screening method for trans-2-nonenal odor suppressors according to the present invention is designed such that test substances are screened with olfactory receptor polypeptides responsive to trans-2-nonenal to select candidate substances for trans-2-nonenal odor suppressors. This method is characterized by comprising the following steps:

adding a test substance and trans-2-nonenal to at least one olfactory receptor polypeptide selected from the group consisting of (a) OR1D2, OR2C1, OR2J2, OR4E2, OR5P3 and OR52N2, and (b) polypeptides which comprise an amino acid sequence sharing an identity of at least 80% with the amino acid sequence of any of the polypeptides in (a) and which are responsive to trans-2-nonenal;

measuring the response of the olfactory receptor polypeptide to trans-2-nonenal; and identifying a test substance that suppresses the response of the olfactory receptor polypeptide on the basis of the measured response.

According to a preferred embodiment of the present invention, the screening method for trans-2-nonenal odor suppressors comprises the following steps:
(i) bringing an olfactory receptor polypeptide selected from the group consisting of (a) OR1D2, OR2C1, OR2J2, OR4E2, OR5P3 and OR52N2, and (b) polypeptides which comprise an amino acid sequence sharing an identity of 80% or more with the amino acid sequence of any of the polypeptides in (a) and which are responsive to trans-2-nonenal into contact with trans-2-nonenal to measure the response of the olfactory receptor polypeptide to trans-2-nonenal;
(ii) mixing a test substance with trans-2-nonenal to measure the response of the olfactory receptor polypeptide used in step (i); and
(iii) comparing the results measured in steps (i) and (ii) to select a test substance causing a reduction in the response as a candidate substance for trans-2-nonenal odor suppressors.

The screening method for trans-2-nonenal odor suppressors according to the present invention is configured such that candidate substances for trans-2-nonenal odor suppressors are selected from among test substances on the basis of the responsiveness of each test substance to an olfactory receptor polypeptide selected from the group consisting of OR1D2, OR2C1, OR2J2, OR4E2, OR5P3, OR52N2, and polypeptides which comprise amino acid sequences sharing an identity of 80% or more with the amino acid sequences of these polypeptides and which are responsive to substances responsible for the characteristic body odor of elderly people.

In the screening method for trans-2-nonenal odor suppressors according to the present invention, the term "test substance" is not limited in any way, but it refers to a subject to be tested for its suppressive effect on trans-2-nonenal odor and is intended to mean a compound, a composition or a mixture. Likewise, the term "trans-2-nonenal odor suppressor" is not limited in any way, but it is intended to mean a compound, a composition or a mixture, which is capable of suppressing trans-2-nonenal odor. Likewise, the term "trans-2-nonenal odor" is intended to mean an odor originating from trans-2-nonenal, as exemplified by the characteristic body odor of elderly people, off-flavors, etc. An explanation will be given below of each step.

<Step (i)>

In step (i), an olfactory receptor polypeptide selected from the group consisting of OR1D2, OR2C1, OR2J2, OR4E2, OR5P3, OR52N2, and polypeptides which comprise an amino acid sequence sharing an identity of 80% or more with the amino acid sequence of any of these polypeptides and which are responsive to trans-2-nonenal is brought into contact with trans-2-nonenal to measure the response of the olfactory receptor polypeptide to trans-2-nonenal.

The olfactory receptor polypeptide to be used for this purpose is an olfactory receptor polypeptide selected from the group consisting of OR1D2, OR2C1, OR2J2, OR4E2, OR5P3, OR52N2, and polypeptides which comprise an amino acid sequence sharing an identity of 80% or more with the amino acid sequence of any of these polypeptides and which are responsive to trans-2-nonenal.

OR2C1 has been registered in GenBank under NM_012368 and is a polypeptide consisting of an amino acid sequence (SEQ ID NO: 2) encoded by DNA having the nucleotide sequence shown in SEQ ID NO: 1.

OR2J2 has been registered in GenBank under NM_030905 and is a polypeptide consisting of an amino acid sequence (SEQ ID NO: 4) encoded by DNA having the nucleotide sequence shown in SEQ ID NO: 3.

OR4E2 has been registered in GenBank under NM_001001912 and is a polypeptide consisting of an amino acid sequence (SEQ ID NO: 6) encoded by DNA having the nucleotide sequence shown in SEQ ID NO: 5.

OR5P3 has been registered in GenBank under NM_153445 and is a polypeptide consisting of an amino acid sequence (SEQ ID NO: 8) encoded by DNA having the nucleotide sequence shown in SEQ ID NO: 7.

OR1D2 has been registered in GenBank under NM_002548 and is a polypeptide consisting of an amino acid sequence (SEQ ID NO: 10) encoded by DNA having the nucleotide sequence shown in SEQ ID NO: 9.

OR52N2 has been registered in GenBank under NM_001005174 and is a polypeptide consisting of an amino acid sequence (SEQ ID NO: 12) encoded by DNA having the nucleotide sequence shown in SEQ ID NO: 11.

Since these polypeptides strongly respond selectively to trans-2-nonenal, the screening method using OR1D2, OR2C1, OR2J2, OR4E2, OR5P3 and/or OR52N2 can be expected to contribute to the development of trans-2-nonenal odor suppressors.

As an olfactory receptor, it is also possible to use an olfactory receptor polypeptide selected from the group consisting of polypeptides which comprise an amino acid sequence sharing an identity of 80% or more, preferably 85% or more, more preferably 90% or more, even more preferably 95% or more, and particularly preferably 98% or more with the amino acid sequence possessed by any of these polypeptides (i.e., SEQ ID NO: 2, 4, 6, 8, 10 or 12) and which are responsive to trans-2-nonenal.

Such olfactory receptor polypeptides may be used alone, or two or more of them may be used in combination.

In the present invention, there is no particular limitation on how to contact an olfactory receptor polypeptide with trans-2-nonenal to measure the response of the olfactory receptor polypeptide to trans-2-nonenal. For example, the response of the olfactory receptor polypeptide may be measured by being contacted with trans-2-nonenal on cells isolated from a living body expressing the olfactory receptor polypeptide, or alternatively, the response of the olfactory receptor polypeptide may be measured by being contacted with trans-2-nonenal on cells genetically engineered to artificially express the olfactory receptor polypeptide. The time required to contact the olfactory receptor polypeptide with trans-2-nonenal is not determined exactly because of also depending on the concentration of trans-2-nonenal, but it is usually 2 to 4 hours. The same goes for when the olfactory receptor polypeptide is contacted with trans-2-nonenal in admixture with a test substance.

Cells genetically engineered to artificially express the olfactory receptor polypeptide may be prepared when cells are transformed with a vector carrying a gene encoding the olfactory receptor polypeptide.

In a preferred embodiment of the present invention, the N-terminal 20 amino acid residues of bovine rhodopsin may be integrated together with the olfactory receptor polypeptide. Upon integration of the N-terminal 20 amino acid residues of bovine rhodopsin, cell membrane expression of the olfactory receptor polypeptide may be facilitated.

Bovine rhodopsin has been registered in GenBank under NM_001014890. Bovine rhodopsin is a polypeptide consisting of an amino acid sequence (SEQ ID NO: 22) encoded by DNA at positions 1 to 1047 of the nucleotide sequence shown in SEQ ID NO: 21.

Moreover, instead of bovine rhodopsin, it is possible to use a polypeptide which comprises an amino acid sequence sharing an identity of 80% or more, preferably 85% or more, more preferably 90% or more, even more preferably 95% or more, and particularly preferably 98% or more with the amino acid sequence shown in SEQ ID NO: 22 and which is capable of facilitating cell membrane expression of the olfactory receptor polypeptide.

It should be noted that amino acid residues of not only bovine rhodopsin but also any other polypeptides may be used as long as they can facilitate cell membrane expression of the olfactory receptor polypeptide.

There is no particular limitation on how to measure the response of the olfactory receptor polypeptide, and any technique used in the art may be used for this purpose. For example, it is known that once an odorous compound has bound to an olfactory receptor polypeptide, G protein in cells will be activated and this G protein will in turn activate adenylate cyclase to convert ATP into cyclic AMP (cAMP), thereby increasing the intracellular level of cAMP. Thus, the response of the olfactory receptor polypeptide can be measured when the level of cAMP is measured. The level of cAMP may be measured using ELISA techniques, reporter gene assay techniques, etc. Above all, it is preferred that the response of the olfactory receptor polypeptide is measured by reporter gene assay techniques using a luminophore (e.g., luciferase).

According to one embodiment of the present invention, the response of the olfactory receptor polypeptide may be evaluated on the basis of the fold increase value determined by dividing the results measured in the presence of trans-2-nonenal by the results measured in the absence of trans-2-nonenal. For example, when the response of the olfactory receptor polypeptide is measured by reporter gene assay techniques using a luminophore (e.g., luciferase), evaluation can be made using trans-2-nonenal at a concentration which gives a fold increase value of preferably 2 or more, more preferably 4 or more, and even more preferably 10 or more.

<Step (ii)>

In step (ii), a test substance is mixed with trans-2-nonenal to measure the response of the olfactory receptor used in step (i).

The response of the olfactory receptor polypeptide may be measured in the same manner as shown in step (i), except that trans-2-nonenal is mixed with the test substance and contacted with the olfactory receptor polypeptide. For example, the response of the olfactory receptor polypeptide may be measured on cells isolated from a living body expressing the olfactory receptor polypeptide, or alternatively, the response of the olfactory receptor polypeptide may be measured on cells genetically engineered to artificially express the olfactory receptor polypeptide. For proper comparison of the results measured in steps (i) and (ii), the measurement conditions in steps (i) and (ii) are preferably the same, except for the presence or absence of the test substance.

<Step (iii)>

In step (iii), the results measured in steps (i) and (ii) are compared with each other to select a test substance causing a reduction in the response as a candidate substance for trans-2-nonenal odor suppressors.

In the present invention, when a reduction in the response is observed as a result of comparing the results measured in steps (i) and (ii), the test substance used in step (ii) can be evaluated as a candidate substance for trans-2-nonenal odor suppressors.

In such a way as described above, test substances can be screened to select candidate substances for trans-2-nonenal odor suppressors. According to the present invention, it is possible to select candidate substances for trans-2-nonenal odor suppressors from among many test substances, without causing any problems such as olfactory fatigue and variations among individuals associated with sensory testing by means of the human olfactory sense.

The selected substances can be used as candidate substances for trans-2-nonenal odor suppressors. If necessary, the selected substances may be subjected to modifications or the like to thereby develop novel compounds having the most suitable odor. Further, the selected substances may be blended with other aroma ingredients to thereby develop aroma ingredients capable of suppressing trans-2-nonenal odor and also having the most suitable odor. The screening method of the present invention can be used to contribute to the development of new aroma ingredients serving as trans-2-nonenal odor suppressors.

3. Screening Method for Trans-2-Octenal Odor Suppressors

The screening method for trans-2-octenal odor suppressors according to the present invention is designed such that test substances are screened with olfactory receptor polypeptides responsive to trans-2-octenal to select candidate substances for trans-2-octenal odor suppressors. This method is characterized by comprising the following steps:

adding a test substance and trans-2-octenal to at least one olfactory receptor polypeptide selected from the group consisting of (a) OR2C1, OR2J2, OR2J3, OR4E2, OR5P3, OR7G1, OR9I1 and OR51A7, and (b) polypeptides which comprise an amino acid sequence sharing an identity of at least 80% with the amino acid sequence of any of the polypeptides in (a) and which are responsive to trans-2-octenal;

measuring the response of the olfactory receptor polypeptide to trans-2-octenal; and identifying a test substance that suppresses the response of the olfactory receptor polypeptide on the basis of the measured response.

According to a preferred embodiment of the present invention, the screening method for trans-2-octenal odor suppressors comprises the following steps:

(i) bringing an olfactory receptor polypeptide selected from the group consisting of (a) OR2C1, OR2J2, OR2J3, OR4E2, OR5P3, OR7G1, OR9I1 and OR51A7, and (b) polypeptides which comprise an amino acid sequence sharing an identity of 80% or more with the amino acid sequence of any of the polypeptides in (a) and which are responsive to trans-2-octenal into contact with trans-2-octenal to measure the response of the olfactory receptor polypeptide to trans-2-octenal;

(ii) mixing a test substance with trans-2-octenal to measure the response of the olfactory receptor polypeptide used in step (i); and (iii) comparing the results measured in steps (i) and (ii) to select a test substance causing a reduction in the response as a candidate substance for trans-2-octenal odor suppressors.

The screening method for trans-2-octenal odor suppressors according to the present invention is configured such that candidate substances for trans-2-octenal odor suppressors are selected from among test substances on the basis of the responsiveness of each test substance to an olfactory receptor polypeptide selected from the group consisting of OR2C1, OR2J2, OR2J3, OR4E2, OR5P3, OR7G1, OR9I1, OR51A7, and polypeptides which comprise amino acid sequences sharing an identity of 80% or more with the amino acid sequences of these polypeptides and which are responsive to trans-2-octenal.

In the screening method for trans-2-octenal odor suppressors according to the present invention, the term "test substance" is not limited in any way, but it refers to a subject to be tested for its suppressive effect on trans-2-octenal odor and is intended to mean a compound, a composition or a mixture. Likewise, the term "trans-2-octenal odor suppressor" is not limited in any way, but it is intended to mean a compound, a composition or a mixture, which is capable of suppressing trans-2-octenal odor. Likewise, the term "trans-2-octenal odor" is intended to mean an odor originating from trans-2-octenal, as exemplified by the characteristic body odor of elderly people, off-flavors, etc. An explanation will be given below of each step.

<Step (i)>

In step (i), an olfactory receptor polypeptide selected from the group consisting of OR2C1, OR2J2, OR2J3, OR4E2, OR5P3, OR7G1, OR9I1, OR51A7, and polypeptides which comprise an amino acid sequence sharing an identity of 80% or more with the amino acid sequence of any of these polypeptides and which are responsive to trans-2-octenal is brought into contact with trans-2-octenal to measure the response of the olfactory receptor polypeptide to trans-2-octenal.

The olfactory receptor polypeptide to be used for this purpose is an olfactory receptor polypeptide selected from the group consisting of OR2C1, OR2J2, OR2J3, OR4E2, OR5P3, OR7G1, OR9I1, OR51A7, and polypeptides which comprise an amino acid sequence sharing an identity of 80% or more with the amino acid sequence of any of these polypeptides and which are responsive to trans-2-octenal.

OR2C1 has been registered in GenBank under NM_012368 and is a polypeptide consisting of an amino acid sequence (SEQ ID NO: 2) encoded by DNA having the nucleotide sequence shown in SEQ ID NO: 1.

OR2J2 has been registered in GenBank under NM_030905 and is a polypeptide consisting of an amino acid sequence (SEQ ID NO: 4) encoded by DNA having the nucleotide sequence shown in SEQ ID NO: 3.

OR4E2 has been registered in GenBank under NM_001001912 and is a polypeptide consisting of an amino acid sequence (SEQ ID NO: 6) encoded by DNA having the nucleotide sequence shown in SEQ ID NO: 5.

OR5P3 has been registered in GenBank under NM_153445 and is a polypeptide consisting of an amino acid sequence (SEQ ID NO: 8) encoded by DNA having the nucleotide sequence shown in SEQ ID NO: 7.

OR2J3 has been registered in GenBank under NM_001005216 and is a polypeptide consisting of an amino acid sequence (SEQ ID NO: 14) encoded by DNA having the nucleotide sequence shown in SEQ ID NO: 13.

OR7G1 has been registered in GenBank under NM_001005192 and is a polypeptide consisting of an amino acid sequence (SEQ ID NO: 16) encoded by DNA having the nucleotide sequence shown in SEQ ID NO: 15.

OR9I1 has been registered in GenBank under NM_001005211 and is a polypeptide consisting of an amino acid sequence (SEQ ID NO: 18) encoded by DNA having the nucleotide sequence shown in SEQ ID NO: 17.

OR51A7 has been registered in GenBank under NM_001004749 and is a polypeptide consisting of an amino acid sequence (SEQ ID NO: 20) encoded by DNA having the nucleotide sequence shown in SEQ ID NO: 19.

Since these polypeptides strongly respond selectively to trans-2-octenal, the screening method using OR2C1, OR2J2, OR2J3, OR4E2, OR5P3, OR7G1, OR9I1 and/or OR51A7 can be expected to contribute to the development of trans-2-octenal odor suppressors.

As an olfactory receptor, it is also possible to use an olfactory receptor polypeptide selected from the group consisting of polypeptides which comprise an amino acid sequence sharing an identity of 80% or more, preferably 85% or more, more preferably 90% or more, even more preferably 95% or more, and particularly preferably 98% or more with the amino acid sequence possessed by any of these polypeptides (i.e., SEQ ID NO: 2, 4, 6, 8, 14, 16, 18 or 20) and which are responsive to trans-2-octenal.

Such olfactory receptor polypeptides may be used alone, or two or more of them may be used in combination.

In the present invention, there is no particular limitation on how to contact an olfactory receptor polypeptide with trans-2-octenal to measure the response of the olfactory receptor polypeptide to trans-2-octenal. For example, the response of the olfactory receptor polypeptide may be measured by being contacted with trans-2-octenal on cells isolated from a living body expressing the olfactory receptor polypeptide, or alternatively, the response of the olfactory receptor polypeptide may be measured by being contacted with trans-2-octenal on cells genetically engineered to artificially express the olfactory receptor polypeptide. The time required to contact the olfactory receptor polypeptide with trans-2-octenal is not determined exactly because of also depending on the concentration of trans-2-octenal, but it is usually 2 to 4 hours. The same goes for when the olfactory receptor polypeptide is contacted with trans-2-octenal in admixture with a test substance.

Cells genetically engineered to artificially express the olfactory receptor polypeptide may be prepared when cells are transformed with a vector carrying a gene encoding the olfactory receptor polypeptide.

In a preferred embodiment of the present invention, the N-terminal 20 amino acid residues of bovine rhodopsin may be integrated together with the olfactory receptor polypeptide. Upon integration of the N-terminal 20 amino acid residues of bovine rhodopsin, cell membrane expression of the olfactory receptor polypeptide may be facilitated.

Bovine rhodopsin has been registered in GenBank under NM_001014890. Bovine rhodopsin is a polypeptide consisting of an amino acid sequence (SEQ ID NO: 22) encoded by DNA at positions 1 to 1047 of the nucleotide sequence shown in SEQ ID NO: 21.

Moreover, instead of bovine rhodopsin, it is possible to use a polypeptide which comprises an amino acid sequence sharing an identity of 80% or more, preferably 85% or more, more preferably 90% or more, even more preferably 95% or more, and particularly preferably 98% or more with the amino acid sequence shown in SEQ ID NO: 22 and which is capable of facilitating cell membrane expression of the olfactory receptor polypeptide.

It should be noted that amino acid residues of not only bovine rhodopsin but also any other polypeptides may be used as long as they can facilitate cell membrane expression of the olfactory receptor polypeptide.

There is no particular limitation on how to measure the response of the olfactory receptor polypeptide, and any technique used in the art may be used for this purpose. For example, it is known that once an odorous compound has bound to an olfactory receptor polypeptide, G protein in cells will be activated and this G protein will in turn activate adenylate cyclase to convert ATP into cyclic AMP (cAMP), thereby increasing the intracellular level of cAMP. Thus, the response of the olfactory receptor polypeptide can be measured when the level of cAMP is measured. The level of cAMP may be measured using ELISA techniques, reporter gene assay techniques, etc. Above all, it is preferred that the response of the olfactory receptor polypeptide is measured by reporter gene assay techniques using a luminophore (e.g., luciferase).

According to one embodiment of the present invention, the response of the olfactory receptor polypeptide may be evaluated on the basis of the fold increase value determined by dividing the results measured in the presence of trans-2-octenal by the results measured in the absence of trans-2-octenal. For example, when the response of the olfactory receptor polypeptide is measured by reporter gene assay techniques using a luminophore (e.g., luciferase), evaluation can be made using trans-2-octenal at a concentration which gives a fold increase value of preferably 2 or more, more preferably 4 or more, and even more preferably 10 or more.

<Step (ii)>

In step (ii), a test substance is mixed with trans-2-octenal to measure the response of the olfactory receptor used in step (i).

The response of the olfactory receptor polypeptide may be measured in the same manner as shown in step (i), except that trans-2-octenal is mixed with the test substance and contacted with the olfactory receptor polypeptide. For example, the response of the olfactory receptor polypeptide may be measured on cells isolated from a living body expressing the olfactory receptor polypeptide, or alternatively, the response of the olfactory receptor polypeptide may be measured on cells genetically engineered to artificially express the olfactory receptor polypeptide. For proper comparison of the results measured in steps (i) and (ii), the measurement conditions in steps (i) and (ii) are preferably the same, except for the presence or absence of the test substance.

<Step (iii)>

In step (iii), the results measured in steps (i) and (ii) are compared with each other to select a test substance causing a reduction in the response as a candidate substance for trans-2-octenal odor suppressors.

In the present invention, when a reduction in the response is observed as a result of comparing the results measured in steps (i) and (ii), the test substance used in step (ii) can be evaluated as a candidate substance for trans-2-octenal odor suppressors.

In such a way as described above, test substances can be screened to select candidate substances for trans-2-octenal odor suppressors. According to the present invention, it is possible to select candidate substances for trans-2-octenal odor suppressors from among many test substances, without causing any problems such as olfactory fatigue and variations among individuals associated with sensory testing by means of the human olfactory sense.

The selected substances can be used as candidate substances for trans-2-octenal odor suppressors. If necessary, the selected substances may be subjected to modifications or the like to thereby develop novel compounds having the most suitable odor. Further, the selected substances may be blended with other aroma ingredients to thereby develop aroma ingredients capable of suppressing trans-2-octenal odor and also having the most suitable odor. The screening method of the present invention can be used to contribute to the development of new aroma ingredients serving as trans-2-octenal odor suppressors.

EXAMPLES

The present invention will be further described in more detail below by way of the following illustrative examples, although the present invention is not limited to these examples.

Example 1

Search for Olfactory Receptor Polypeptides Responding to Trans-2-Nonenal (1) Cloning of Olfactory Receptor Genes Human olfactory receptor genes were obtained by PCR cloning with Human Genomic DNA: Female (Promega) on the basis of their sequence information registered in GenBank. Into pME18S vectors, the N-terminal 20 amino acid residues of bovine rhodopsin were integrated, and subsequently the resulting human olfactory receptor genes were integrated respectively downstream thereof to obtain human olfactory receptor gene expression vectors.

(2) Expression of Olfactory Receptor Genes in HEK293T Cells

Each human olfactory receptor gene expression vector (0.05 µg), RTP1S vector (0.01 µg), firefly luciferase vector pGL4.29 containing a cAMP responsive element promoter (Promega, 0.01 µg) and Renilla luciferase vector pGL4.74 containing a thymidine kinase promoter (Promega, 0.005 µg) were dissolved in 10 µL of Opti-MEM I (gibco) to give a gene solution (for one well). HEK293T cells were seeded in 100 µL volumes into 96-well plates (Biocoat, Corning) at a cell density reaching confluence after 24 hours, and the gene solutions were added to the respective wells to cause gene transfer into the cells by lipofection techniques in accordance with the usage of Lipofectamine 3000, followed by culture at 37° C. under a 5% carbon dioxide atmosphere for 24 hours.

(3) Luciferase Reporter Gene Assay

After removal of the culture solutions, an odorous substance serving as an analyte, which had been prepared at a given concentration with CD293 (gibco) medium (supplemented with 20 µM L-glutamine), was added in 50 µL volumes to stimulate the cells for 3 hours, followed by luciferase activity measurement in accordance with the usage of a Dual-Luciferase Reporter Assay System (Promega). The response intensity of each olfactory receptor polypeptide was expressed as a fold increase value, which was determined by dividing the luciferase activity generated upon stimulation with the odorous substance by the luciferase activity generated in a test system not containing the odorous substance.

(4) Identification of Olfactory Receptor Polypeptides Responding to Trans-2-Nonenal The cells engineered to express 402 types of human olfactory receptors were measured for receptor responses to trans-2-nonenal (60 µM) by the luciferase reporter gene assay. The results obtained are shown in FIG. 1. OR1D2, OR2C1, OR2J2, OR4E2, OR5P3 and OR52N2 were found to respond to trans-2-nonenal with a fold increase value of 2 or more.

In addition, OR1D2, OR2C1, OR2J2, OR4E2, OR5P3 and OR52N2 were measured for their receptor response to different concentrations of trans-2-nonenal by the luciferase reporter gene assay. The results obtained are shown in FIGS. 2 to 7, respectively. OR1D2, OR2C1, OR2J2, OR4E2, OR5P3 and OR52N2 were found to respond to trans-2-nonenal in a concentration-dependent manner. On the other hand, no response was observed in each mock test. Namely, OR1D2, OR2C1, OR2J2, OR4E2, OR5P3 and OR52N2 were shown to respond specifically to trans-2-nonenal.

Example 2

Search for Olfactory Receptor Polypeptides Responding to Trans-2-Octenal

Figure 8:
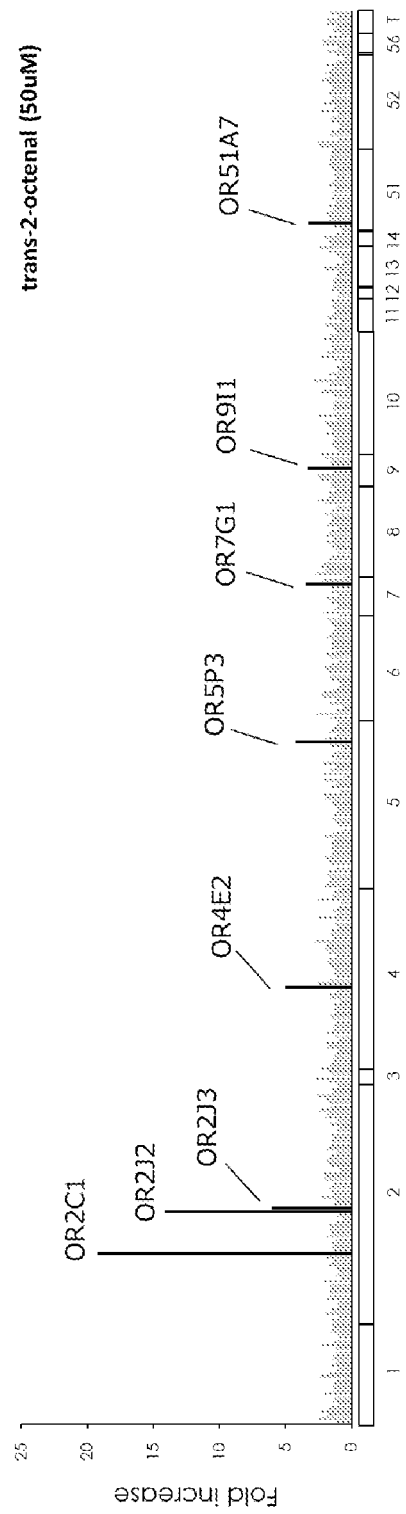
FIG. 8 shows the results measured for the responses of various olfactory receptor polypeptides to trans-2-octenal.

In the same manner as shown in Example 1, the cells engineered to express 402 types of human olfactory receptors were measured for receptor responses to trans-2-octenal (50 μM) by the luciferase reporter gene assay. The results obtained are shown in FIG. 8. OR2C1, OR2J2, OR2J3, OR4E2, OR5P3, OR7G1, OR9I1 and OR51A7 were found to respond to trans-2-octenal with a fold increase value of 2 or more.

Example 3

Figure 9:
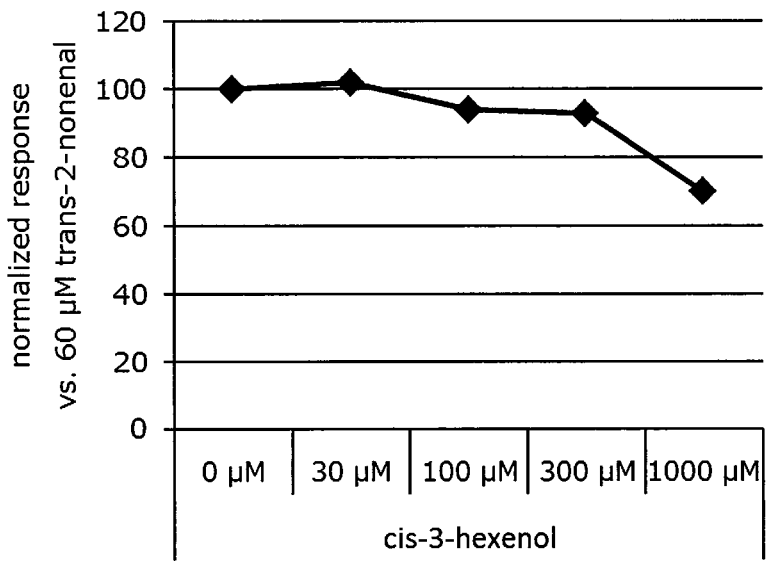
FIG. 9 shows the results obtained for the suppressive effect induced by addition of cis-3-hexenol on the response of olfactory receptor OR2C1 to trans-2-nonenal.
Figure 10:
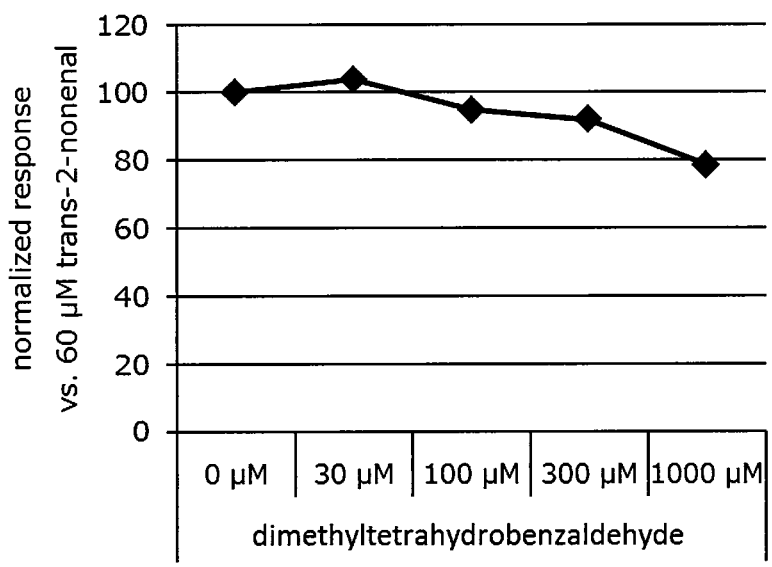
FIG. 10 shows the results obtained for the suppressive effect induced by addition of dimethyltetrahydrobenzaldehyde on the response of olfactory receptor OR2C1 to trans-2-nonenal.

Evaluation of Materials that Suppress the Characteristic Body Odor of Elderly People for their Suppressive Effect on the Response of OR2C1 cis-3-Hexenol and dimethyltetrahydrobenzaldehyde (IFF trade name: Triplal), which had been known to mask and modulate the characteristic body odor of elderly people, i.e., known as materials that suppress the characteristic body odor of elderly people in Journal of Society Cosmetic Chemists Japan, 34(4), 379-386 (2000), were measured for their suppressive effect on the response of OR2C1 strongly responsive to trans-2-nonenal by the luciferase reporter gene assay. In the luciferase reporter gene assay, trans-2-nonenal and each material that suppresses the characteristic body odor of elderly people were mixed for use as an analyte, and the ratio of the fold increase value obtained in the test using the material that suppresses the characteristic body odor of elderly people was determined assuming that the fold increase value obtained in the test without using the material that suppresses the characteristic body odor of elderly people was set to 100. The results obtained are shown in FIGS. 9 and 10, respectively. cis-3-Hexenol and dimethyl-tetrahydrobenzaldehyde showed the effect of reducing the response of OR2C1 to trans-2-nonenal in a concentration-dependent manner.

INDUSTRIAL APPLICABILITY

The screening method of the present invention allows selection of respective candidate substances for materials that suppress the characteristic body odor of elderly people, trans-2-nonenal odor suppressors and trans-2-octenal odor suppressors from among many test substances. The screening method of the present invention can be expected to contribute to the development of materials that suppress the characteristic body odor of elderly people, and further trans-2-nonenal odor suppressors and trans-2-octenal odor suppressors.

The invention claimed is:

1. A screening method for materials that suppress the characteristic body odor of elderly people, which comprises the following steps:
    adding a test substance and a substance responsible for the characteristic body odor of elderly people to at least one olfactory receptor polypeptide, wherein said olfactory receptor polypeptide is selected from the group consisting of OR2C1 that comprises the amino acid sequence of SEQ ID NO: 2, OR2J2 that comprises the amino acid sequence of SEQ ID NO: 4, OR4E2 that comprises the amino acid sequence of SEQ ID NO: 6, and OR5P3 that comprises the amino acid sequence of SEQ ID NO: 8, or wherein said olfactory receptor polypeptide is selected from the group consisting of polypeptides which comprise an amino acid sequence that shares at least 95% sequence identity with the amino acid sequence of SEQ ID NO: 2, 4, 6, or 8 and which are responsive to the substance responsible for the characteristic body odor of elderly people;
    measuring the response of the olfactory receptor polypeptide to the substance responsible for the characteristic body odor of elderly people; and
    identifying a test substance that suppresses the response of the olfactory receptor polypeptide on the basis of the measured response, wherein the substance responsible for the characteristic body odor of elderly people is at least one selected from the group consisting of trans-2-nonenal and trans-2-octenal.

2. The method according to claim 1, wherein the response of the olfactory receptor polypeptide is measured on cells isolated from a living body expressing the olfactory receptor polypeptide or on cells genetically engineered to artificially express the olfactory receptor polypeptide.

3. The method according to claim 1, wherein the response of the olfactory receptor polypeptide is measured by a reporter assay.

4. A screening method for trans-2-nonenal odor suppressors, which comprises the following steps:
    adding a test substance and trans-2-nonenal to at least one olfactory receptor polypeptide, wherein said olfactory receptor polypeptide is selected from the group consisting of OR2C1 that comprises the amino acid sequence of SEQ ID NO: 2, OR2J2 that comprises the amino acid sequence of SEQ ID NO: 4, OR4E2 that comprises the amino acid sequence of SEQ ID NO: 6, OR5P3 that comprises the amino acid sequence of SEQ ID NO: 8, OR1D2 comprises the amino acid sequence of SEQ ID NO:10, and OR52N2 that comprises the amino acid sequence of SEQ ID NO: 12, or wherein said olfactory receptor polypeptide is selected from the group consisting of polypeptides which comprise an amino acid sequence that shares at least 95% sequence identity with the amino acid sequence of SEQ ID NO: 2, 4, 6, 8, 10 or 12 and which are responsive to trans-2-nonenal;
    measuring the response of the olfactory receptor polypeptide to trans-2-nonenal; and
    identifying a test substance that suppresses the response of the olfactory receptor polypeptide on the basis of the measured response.

5. The method according to claim 4, wherein the response of the olfactory receptor polypeptide is measured on cells isolated from a living body expressing the olfactory receptor polypeptide or on cells genetically engineered to artificially express the olfactory receptor polypeptide.

6. The method according to claim 4, wherein the response of the olfactory receptor polypeptide is measured by a reporter assay.

7. A screening method for trans-2-octenal odor suppressors, which comprises the following steps:
   adding a test substance and trans-2-octenal to at least one olfactory receptor polypeptide, wherein said olfactory receptor polypeptide is selected from the group consisting of OR2C1 that comprises the amino acid sequence of SEQ ID NO: 2, OR2J2 that comprises the amino acid sequence of SEQ ID NO: 4, OR4E2 that comprises the amino acid sequence of SEQ ID NO: 6, OR5P3 that comprises the amino acid sequence of SEQ ID NO: 8, OR2J3 that comprises the amino acid sequence of SEQ ID NO:14, OR7G1 that comprises the amino acid sequence of SEQ ID NO:16, OR9I1 that comprises the amino acid sequence of SEQ ID NO: 18, and OR51A7 that comprises the amino acid sequence of SEQ ID NO: 20, or wherein said olfactory receptor polypeptide is selected from the group consisting of polypeptides which comprise an amino acid sequence that shares at least 95% sequence identity with the amino acid sequence of SEQ ID NO: 2, 4, 6, 8, 14, 16, 18, and 20 and which are responsive to trans-2-octenal;
   measuring the response of the olfactory receptor polypeptide to trans-2-octenal; and
   identifying a test substance that suppresses the response of the olfactory receptor polypeptide on the basis of the measured response.

8. The method according to claim 7, wherein the response of the olfactory receptor polypeptide is measured on cells isolated from a living body expressing the olfactory receptor polypeptide or on cells genetically engineered to artificially express the olfactory receptor polypeptide.

9. The method according to claim 7, wherein the response of the olfactory receptor polypeptide is measured by a reporter assay.

* * * * *